United States Patent
Ting et al.

(10) Patent No.: US 8,367,358 B2
(45) Date of Patent: *Feb. 5, 2013

(54) REAGENT, KIT AND METHOD FOR DIFFERENTIATING AND COUNTING LEUKOCYTES

(75) Inventors: Lei Ting, Shenzhen (CN); Xu Bing, Shenzhen (CN); Kuang Yuji, Shenzhen (CN); Zhang Baohua, Shenzhen (CN); Shao Jianhui, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 401 days.

This patent is subject to a terminal disclaimer.

(21) Appl. No.: 12/568,500

(22) Filed: Sep. 28, 2009

(65) Prior Publication Data

US 2010/0151509 A1    Jun. 17, 2010

(30) Foreign Application Priority Data

Dec. 17, 2008 (CN) .......................... 2008 1 0241297

(51) Int. Cl.
  *C07D 403/08*    (2006.01)
  *C12Q 1/68*    (2006.01)
  *G01N 1/30*    (2006.01)
(52) U.S. Cl. ............ 435/14; 435/29; 514/400; 514/408; 514/415; 514/452; 548/455
(58) Field of Classification Search .................. 435/14, 435/29; 514/400, 408, 415, 452; 548/455
See application file for complete search history.

(56) References Cited

U.S. PATENT DOCUMENTS

| | | |
|---|---|---|
| 3,883,274 A | 5/1975 | Vuaille |
| 4,122,348 A | 10/1978 | Bruck |
| 4,146,604 A | 3/1979 | Kleinerman |
| 4,286,963 A | 9/1981 | Ledis et al. |
| 4,325,706 A | 4/1982 | Russell et al. |
| 4,332,785 A | 6/1982 | Robert et al. |
| 4,336,029 A | 6/1982 | Peter |
| 4,414,325 A | 11/1983 | Masuda et al. |
| 4,447,547 A | 5/1984 | Allen et al. |
| 4,485,175 A | 11/1984 | Ledis et al. |
| 4,528,274 A | 7/1985 | Carter et al. |
| 4,529,705 A | 7/1985 | Larsen |
| 4,544,546 A | 10/1985 | Wang et al. |
| 4,571,388 A | 2/1986 | O'Connell et al. |
| 4,596,035 A | 6/1986 | Gershman et al. |
| 4,617,275 A | 10/1986 | Matsuda et al. |
| 4,637,986 A | 1/1987 | Brown et al. |
| 4,707,451 A | 11/1987 | Sage et al. |
| 4,745,071 A | 5/1988 | Lapicola et al. |
| 4,751,179 A | 6/1988 | Ledis et al. |
| 4,822,745 A | 4/1989 | Burns et al. |
| 4,882,284 A | 11/1989 | Kirchanski et al. |
| 4,883,867 A | 11/1989 | Lee et al. |
| 4,933,293 A | 6/1990 | Kuroda et al. |
| 4,957,870 A | 9/1990 | Lee et al. |
| 4,971,917 A | 11/1990 | Kuroda |
| 4,978,624 A | 12/1990 | Cremins et al. |
| 4,981,803 A | 1/1991 | Kuroda |
| 4,985,174 A | 1/1991 | Kuroda et al. |
| 5,039,613 A | 8/1991 | Matsuda et al. |
| 5,075,556 A | 12/1991 | Fan et al. |
| 5,116,539 A | 5/1992 | Hamaguchi et al. |
| 5,155,044 A | 10/1992 | Ledis et al. |
| 5,175,109 A | 12/1992 | Sakata et al. |
| 5,179,026 A | 1/1993 | Matsuda et al. |
| 5,180,677 A | 1/1993 | Di Ianni et al. |
| 5,188,935 A | 2/1993 | Leif et al. |
| 5,227,304 A | 7/1993 | Wong |
| 5,232,857 A | 8/1993 | Lefevre et al. |
| 5,242,832 A | 9/1993 | Sakata |
| 5,250,437 A | 10/1993 | Toda et al. |
| 5,264,369 A | 11/1993 | Sakata et al. |
| 5,284,771 A | 2/1994 | Fan et al. |
| 5,316,725 A | 5/1994 | Carver et al. |
| 5,316,951 A | 5/1994 | Carver et al. |
| 5,321,130 A | 6/1994 | Yue et al. |
| 5,350,695 A | 9/1994 | Colella et al. |
| 5,360,739 A | 11/1994 | Fan et al. |
| 5,389,549 A | 2/1995 | Hamaguchi et al. |
| 5,411,891 A | 5/1995 | Fan et al. |
| 5,413,938 A | 5/1995 | Tsujino et al. |
| 5,438,003 A | 8/1995 | Colella et al. |
| 5,486,477 A | 1/1996 | Carver et al. |
| 5,492,833 A | 2/1996 | Rodriguez et al. |
| 5,496,734 A | 3/1996 | Sakata et al. |

| | | |
|---|---|---|
| 5,510,267 A | 4/1996 | Marshall |
| 5,516,695 A | 5/1996 | Kim et al. |
| 5,518,928 A | 5/1996 | Cremins et al. |
| 5,538,893 A | 7/1996 | Sakata et al. |
| 5,559,037 A | 9/1996 | Kim et al. |
| 5,563,070 A | 10/1996 | Yamamoto et al. |
| 5,616,501 A | 4/1997 | Rodriguez et al. |
| 5,618,733 A * | 4/1997 | Sakata et al. ............ 436/17 |
| 5,633,167 A | 5/1997 | Fan et al. |
| 5,639,630 A | 6/1997 | Malin et al. |
| 5,639,666 A | 6/1997 | Shenkin |
| 5,656,449 A | 8/1997 | Yue |
| 5,677,183 A | 10/1997 | Takarada et al. |
| 5,686,308 A | 11/1997 | Li et al. |
| 5,691,204 A | 11/1997 | Kim et al. |
| 5,731,206 A | 3/1998 | Ledis et al. |
| 5,733,784 A | 3/1998 | Studholme et al. |
| 5,747,343 A | 5/1998 | Tsuchiya et al. |
| 5,763,280 A | 6/1998 | Li et al. |
| 5,773,299 A | 6/1998 | Kim et al. |
| 5,786,224 A | 7/1998 | Li et al. |
| 5,817,518 A | 10/1998 | Li et al. |
| 5,821,127 A | 10/1998 | Akai et al. |
| 5,821,128 A | 10/1998 | Provost |
| 5,840,515 A | 11/1998 | Provost |
| 5,843,608 A | 12/1998 | Li et al. |
| 5,858,667 A | 1/1999 | Dertinger et al. |
| 5,874,311 A | 2/1999 | Li et al. |
| 5,879,900 A | 3/1999 | Kim et al. |
| 5,882,934 A | 3/1999 | Li et al. |
| 5,891,731 A | 4/1999 | Akai et al. |
| 5,928,949 A | 7/1999 | Sakata et al. |
| 5,958,776 A | 9/1999 | Sakata et al. |
| 5,968,832 A | 10/1999 | Uchihashi et al. |
| 5,994,089 A | 11/1999 | Siiman et al. |
| 5,994,138 A | 11/1999 | Veriac |
| 6,004,816 A | 12/1999 | Mizukami et al. |
| 6,060,322 A | 5/2000 | Horton et al. |
| 6,100,038 A | 8/2000 | Dertinger et al. |
| 6,114,130 A | 9/2000 | Veriac et al. |
| 6,114,173 A | 9/2000 | Zelmanovic et al. |
| 6,197,593 B1 | 3/2001 | Deka et al. |
| 6,245,499 B1 | 6/2001 | Suzuki et al. |
| 6,248,319 B1 | 6/2001 | Zsebo et al. |
| 6,271,035 B1 | 8/2001 | Deka et al. |
| 6,287,791 B1 | 9/2001 | Terstappen et al. |
| 6,350,613 B1 | 2/2002 | Wardlaw et al. |
| 6,368,864 B1 | 4/2002 | Deka et al. |
| 6,495,692 B1 | 12/2002 | Wang et al. |
| 6,524,858 B1 | 2/2003 | Zelmanovic et al. |
| 6,551,831 B2 | 4/2003 | Gupta et al. |
| RE38,131 E | 6/2003 | Uchihashi et al. |
| 6,630,990 B2 | 10/2003 | van't Oever et al. |
| 6,632,676 B1 | 10/2003 | Crews et al. |
| 6,664,110 B1 | 12/2003 | Tsuji et al. |
| 6,794,152 B2 | 9/2004 | Ryan et al. |
| 6,869,798 B2 | 3/2005 | Crews et al. |
| 6,900,023 B1 | 5/2005 | Houwen et al. |
| 6,955,872 B2 | 10/2005 | Maples et al. |
| 6,977,156 B2 | 12/2005 | Ryan et al. |
| 7,083,982 B2 | 8/2006 | Wang et al. |
| 7,235,404 B2 | 6/2007 | Lang et al. |
| 7,247,484 B2 | 7/2007 | Wu et al. |
| 7,300,797 B2 | 11/2007 | van Agthoven et al. |
| 7,405,082 B2 | 7/2008 | Mizukami et al. |
| 7,449,337 B2 | 11/2008 | Deka et al. |
| 7,465,584 B2 | 12/2008 | Matsumoto et al. |
| 7,598,385 B2 | 10/2009 | Peng et al. |
| 7,709,653 B2 | 5/2010 | Jianhui |
| 7,960,099 B2 | 6/2011 | Xu et al. |
| 8,067,602 B2 | 11/2011 | Shao |
| 2002/0182623 A1 | 12/2002 | Lefevre et al. |
| 2003/0145394 A1 | 8/2003 | Wang et al. |
| 2004/0241769 A1 | 12/2004 | Crews et al. |
| 2005/0202400 A1 | 9/2005 | Tsuji et al. |
| 2005/0272026 A1 | 12/2005 | Oguni |
| 2006/0177347 A1 | 8/2006 | Larsen et al. |
| 2007/0111276 A1 | 5/2007 | Lefevre et al. |
| 2007/0178597 A1 | 8/2007 | Tsuji et al. |
| 2008/0026475 A1 | 1/2008 | van Agthoven et al. |
| 2008/0131898 A1 | 6/2008 | Tsuji et al. |
| 2008/0176274 A1 | 7/2008 | Tsuji et al. |
| 2009/0017441 A1 | 1/2009 | Peng et al. |
| 2009/0023129 A1 | 1/2009 | Xu et al. |
| 2009/0176270 A1 | 7/2009 | Shao |
| 2010/0178654 A1 | 7/2010 | Kataoka et al. |

FOREIGN PATENT DOCUMENTS

| | | |
|---|---|---|
| CN | 1101980 | 4/1995 |
| CN | 1101982 | 4/1995 |
| CN | 1202621 | 12/1998 |
| CN | 1149397 | 5/2004 |
| EP | 0548983 | 6/1993 |
| EP | 0794435 | 9/1997 |
| WO | WO9717471 | 5/1997 |
| WO | WO03104771 | 12/2003 |

OTHER PUBLICATIONS

Leukocyte definition document (downloaded from the internet on Apr. 25, 2012, Virginia.edu. Aug. 2006, URL: http://web.archive.org/web/20060829205026/http://www.bme.virginia.edu/ley/leukocytes.html).*

Jason A. Bordelon et al., "Viscometry and Atomic Force Microscopy Studies of the Interactions of a Dimeric Cyanine Dye with DNA." J. Phys. Chem. Soc. 2006, 128, pp. 4838-4843.

U.S. Appl. No. 12/482,335, filed Jun. 10, 2009, Shao Jianhui.

U.S. Appl. No. 12/580,474, filed Oct. 16, 2009, Yuji.

Alexandre Fuestenburg et al., "Ultrafast Excited-State Dynamics of DNA Fluorescent Intercalators: New Insight into the Fluorescent Enhancement Mechanism." J. Am. Chem. Soc. 2006, 128, pp. 7661-7669.

L. G. S. Booker et al., "Absorption of Unsymmetrical Carbocyanines." J. Amer. Chem. Soc. 1945, 67, pp. 1889-1893.

Stephen J. Mason et al., "Solid-Phase Catch, Activate, and Release Synthesis of Cyanine Dyes." American Chemical Society Organic Letters 2002, vol. 4 No. 24, pp. 4261-4264.

Notice of Allowance dated Aug. 7, 2009 for U.S. Appl. No. 11/967,991.

Notice of Allowance dated Feb. 22, 2010 for U.S. Appl. No. 12/482,335.

Netzel, T. et al., "Base-Content Dependence of Emission Enhancements, Quantum Yields, and Lifetimes for Cyanine Dyes Bound to Double Strand DNA: Photophysical Properties of Monomeric and Bichromophoric DNA Stains". 1995, J. Phys. Chem., 99, 17936-179474.

Office Action dated May 10, 2011 for U.S. Appl. No. 12/334,274.

Notice of Allowance in U.S. Appl. No. 11/967,897 dated Mar. 10, 2011.

Fei, X. et al., 'Solid-Phase Synthesis and Modification of Thiazole Orange and its Derivatives and Their Spectral Properties'. Journal of Combinatorial Chemistry, vol. 9 (6), p. 945 (last 2 paragraphs), 2007.

Office Action dated Oct. 25, 2011 for U.S. Appl. No. 12/580,474.

Office Action dated Dec. 7, 2011 for U.S. Appl. No. 12/843,671.

Nakamura et al., 'Transition-Metal-Catalyzed Reactions in Heterocyclic Synthesis'. Chem Rev, vol. 104 p. 2127, 2004.

Chattopadhyay et al., 'Formation of Medium-Ring Heterocycles by Diene and Enyne Metathesis'. Tetrahedron vol. 63, p. 3919, 2007.

Dorwold, 'Side Reactions in Organic Synthesis'. Wiley, Preface, 2005.

Notice of Allowance in U.S. Appl. No. 11/967,897 dated Feb. 9, 2011.

Notice of Allowance in U.S. Appl. No. 11/967,991 dated Aug. 7, 2009.

U.S. Appl. No. 12/843,671, dated Jul. 26, 2010, Zhao et al.

Kristine M. Sovenyhazy et al., "Spectroscopic Studies of the Multiple Binding Modes of a Trimethine-Bridged Cyanine Dye with DNA", Nucleic Acids Research, vol. 31 No. 10, 2561-2569, 2003.

* cited by examiner

*Primary Examiner* — Savitha Rao

(74) *Attorney, Agent, or Firm* — Kory D. Christensen; Matthew S. Bethards; Stoel Rives LLP

(57) ABSTRACT

The present disclosure discloses a reagent for differentiating and counting leukocytes which includes: (1) cationic cyanine compounds selected from those having the following general formulae I and II; (2) cationic surfactants selected from those having the following general formulae III, IV and/or V; (3) at least one nonionic surfactant; and (4) optionally, at least one anionic compound selected from those having one or more carboxyl or sulphonyl groups; and optionally includes alcohol compounds. Also disclosed is a kit comprising the reagent for differentiating and counting leukocytes. Further disclosed is a method for differentiating and counting leukocytes using the reagent and kit. Use of the reagent, kit and method disclosed enables the identification of leukocytes in blood samples into five subtypes in a very short time, or at least achieves the differentiation and counting of four leukocyte groupings. Moreover, immature and abnormal cells can be identified.

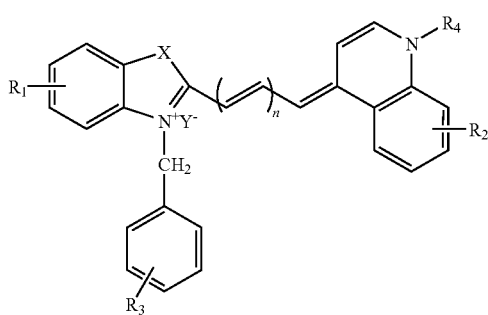

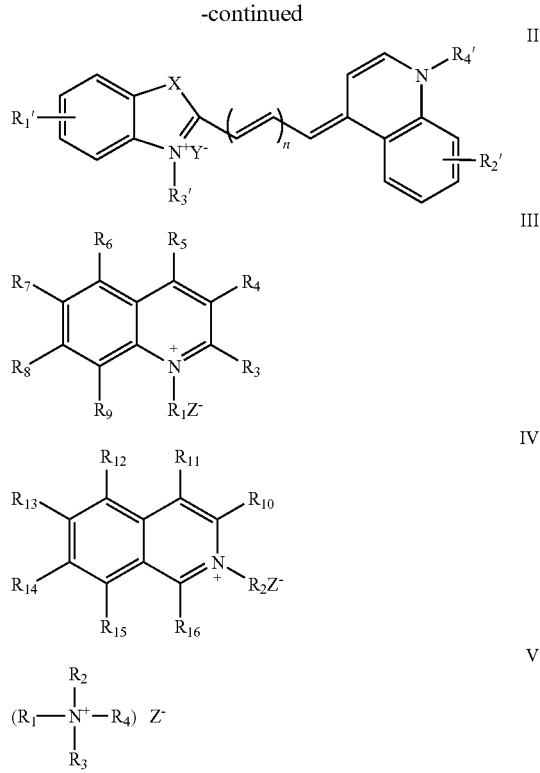

21 Claims, 14 Drawing Sheets

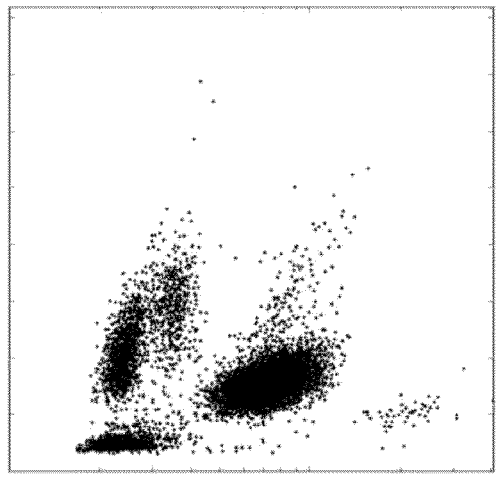 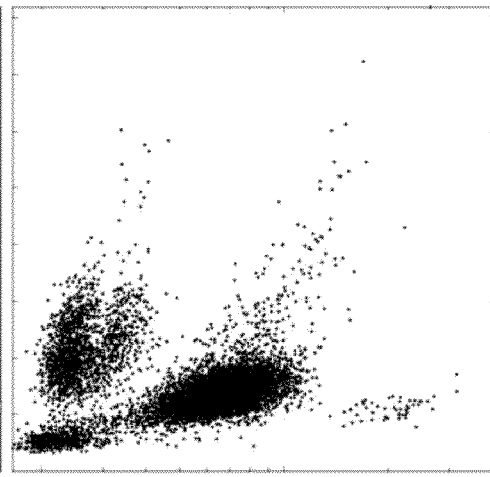
Fig. 6A              Fig. 6B
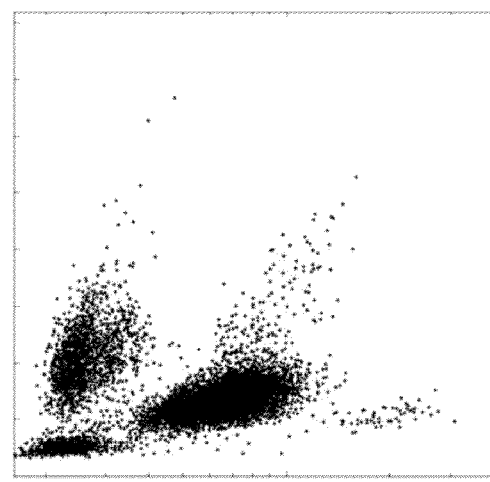 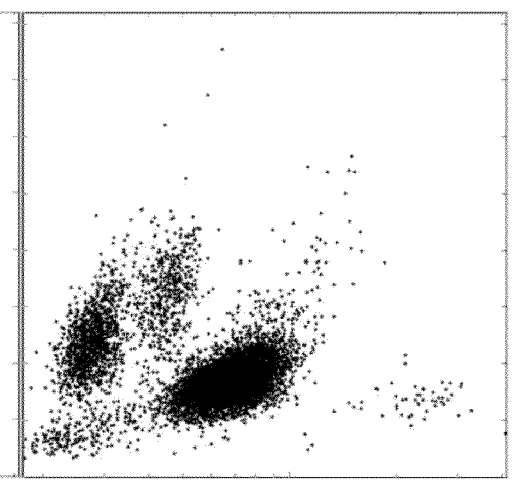
Fig. 6C              Fig. 6D
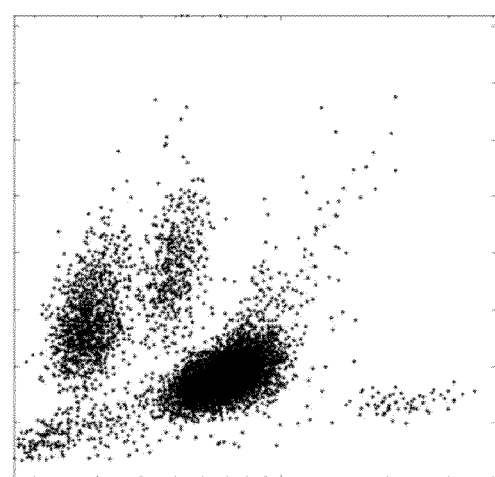 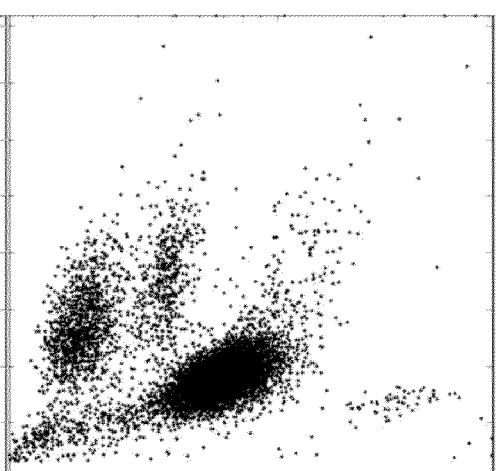
Fig. 6E              Fig. 6F

REAGENT, KIT AND METHOD FOR DIFFERENTIATING AND COUNTING LEUKOCYTES

RELATED APPLICATIONS

This application claims priority to Chinese Patent Application No. 200810241297.5, filed Dec. 17, 2008, for "REAGENT FOR DIFFERENTIATING AND COUNTING LEUKOCYTES, KIT COMPRISING THE SAME AND METHOD FOR DIFFERENTIATING AND COUNTING LEUKOCYTES," and to Chinese Patent Application No. 200910177186.7, filed Sep. 28, 2009, for "REAGENT FOR DIFFERENTIATING AND COUNTING LEUKOCYTES, KIT COMPRISING THE SAME AND METHOD FOR DIFFERENTIATING AND COUNTING LEUKOCYTES," the disclosures of which are fully incorporated herein by reference.

TECHNICAL FIELD

The present disclosure relates to the field of blood detection, more particularly to the differentiation and counting of leukocytes.

BRIEF SUMMARY

The present disclosure relates to a reagent for differentiating and counting leukocytes and a method for differentiating and counting leukocytes. More particularly, the present disclosure relates to a blood analysis reagent for differentiating and counting leukocytes, a kit comprising said reagent and a method for differentiating and counting leukocytes using said reagent or said kit.

BRIEF DESCRIPTION OF THE DRAWINGS

FIGS. 6A-F are scattergrams formed by plotting the side fluorescence intensity against side-scattered light intensity of blood measured using the reagent for differentiating and counting leukocytes according to one embodiment of the present disclosure, wherein FIGS. 6A-C show the detection results for blood samples stored for 4, 36 and 72 hours respectively, obtained using Reagent E with no alcohol added, while FIGS. 6D-F show the detection results for blood samples stored for 4, 36 and 72 hours respectively, obtained using Reagent F with alcohol added. (Example 5).

DETAILED DESCRIPTION

Figure 1:
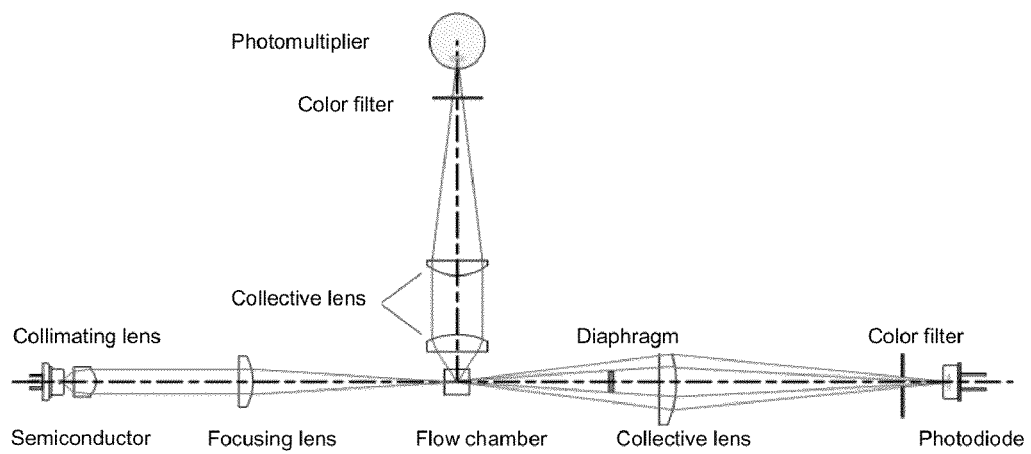
FIG. 1 is a schematic diagram of one embodiment of an optical system of the cell analyzer used in the detection method of the present disclosure.

Human blood cells are generally differentiated into three types: erythrocyte, leukocyte and platelet, and leukocytes can be subdivided into five subtypes: monocyte, lymphocyte and granulocyte (including eosinophil, neutrophil and basophil). Blood cells are generated in bone marrow where they are differentiated from immature cells, grow mature, and migrate to peripheral blood to play their respective functions. The respective subtypes of leukocyte in the peripheral blood of healthy persons are in almost constant proportions. When some diseases occur in the human body, the amount of a certain subtype of leukocyte will increase or decrease. In addition, the venous blood of patients with leukemia, cancer metastasis to bone marrow and severe infection etc., usually has immature leukocytes, typically immature granulocytes, that have a higher DNA content than normal leukocytes and that are not present in the venous blood of normal persons, while patients infected with viruses such as hepatitis virus or cytomegalovirus normally will have abnormal cells, typically abnormal lymphocytes, in their venous blood. Therefore, in clinical laboratories, it is ordinary to differentiate and count leukocytes from the blood of patients, detect for the presence of immature leukocytes and abnormal cells and, if any, count the number thereof, in order to screen for some diseases.

Presently, leukocytes are typically differentiated and counted using automatic hemocyte analyzers in hospitals. In terms of means of detection, the methods for differentiating and counting leukocytes are mainly divided into two types: the impedance method and the laser flow cytometry method, while other means of detection such as radio frequency and direct current are less employed. The differentiation of leukocytes into two or three subtypes are commonly achieved using the impedance method, while the laser flow cytometry method is generally used to effect the identification of leukocytes into five subtypes and the identification of abnormal leukocytes by measuring multiangle scattered light, the amount of fluorescence, the amount of antigen/antibody labels, and combinations thereof to differentiate the leukocytes.

The in-hospital analysis of blood samples from patients involves collecting fresh anti-coagulation blood samples from the body of the patients which are sometimes stored for a period of time before analysis and sometimes saved for a prolonged period of time for possible re-detection. The fresh blood samples age gradually over time, and there will be some changes in cell morphology between the fresh blood and the aged blood from the same blood sample, which may result in a decreased reliability in the differentiation and counting of leukocytes in the aged blood.

Chinese Patent CN95115317.x discloses a method for achieving the differentiation of leukocytes into five subtypes using two kinds of reagents, in which the first reagent that comprises anionic organic compounds such as acidic pigments differentiates leukocytes into four groupings: lymphocyte, monocyte, eosinophil, and basophil plus neutrophil, while the second reagent distinguishes basophils from other blood cell types. Such a method achieves the differentiation of leukocytes into five subtypes by colligating the results from the two reagents. The laser scattering method is used for detection. A relatively longer time for stabilization is required to differentiate basophils using the disclosed method, that is, at least 120 seconds is needed before detection can be conducted, which would limit the detection speed of the analyzer. In addition, said method fails to identify and count immature leukocytes.

U.S. Pat. No. 3,883,247 relates to a method for achieving the differentiation of leukocytes into five subtypes by staining the nucleic acids in leukocytes with fluorescent dyes for heterochromatin such as acridine orange and differentiating the leukocytes in terms of differences in the amounts of red and green fluorescence from various leukocyte subtypes. The acridine orange used in the method is physically toxic and an environmental pollutant. Another disadvantage of the method is the relatively longer staining time required, i.e. from tens of seconds to several minutes, which would limit the detection speed of the analyzer.

U.S. Pat. No. 4,882,284 relates to a method for achieving the differentiation of leukocytes into five subtypes by staining the various kinds of blood cells through a non-hemolytic approach using oxazine fluorescent dyes, and differentiating the leukocytes in terms of the intensities of forward-scattered light, side-scattered light and red fluorescence from different kinds of cells. The method needs to detect erythrocytes, leukocytes and platelets at the same time so that some of the abnormal erythrocytes such as macrocytes would influence the accurate counting of leukocytes.

Chinese Patent application number 88101677 (and whose patent number is CN1018586B), relates to a method for differentiating leukocytes into five subtypes and a reagent system therefor. The method involves fully lysing erythrocytes with an acidic hemolytic agent while maintaining the integrity of the leukocytes, and then differentiating the leukocytes while preventing excess dissolution using a basic salt solution. The detection system employs the light scattering or radio frequency/direct current approach. The method cannot distinguish immature leukocytes from normal leukocytes very well. Moreover, the optimal reaction temperature for differentiation by this method is normal temperature, while the ambient temperature during practical detection tends to change and in turn the detection results will vary, resulting in a decreased accuracy of differentiation and counting. Therefore the method entails the equipping of both a refrigerating device and a heating device to maintain the detection temperature at room temperature in order to avoid the influence of temperature on reaction, which would greatly increase the equipment cost.

Chinese Patent CN97123137.0 relates to a method for differentiating and counting juvenile leukocytes by treating blood samples with a hemolytic agent comprising nonionic surfactants and amino acids to render other leukocytes damaged while keeping juvenile leukocytes alive, and staining the leukocytes with a fluorescent dye to achieve the accurate differentiation and counting of juvenile leukocytes and other leukocytes. However, the method can only differentiate leukocytes into three subtypes, i.e. lymphocyte, monocyte and granulocyte and fails to achieve the differentiation of leukocytes into five subtypes.

In one aspect of the present disclosure there is provided a reagent for differentiating and counting leukocytes which comprises:

(1) Cationic cyanine compounds selected from those having the following general formulae I and II:

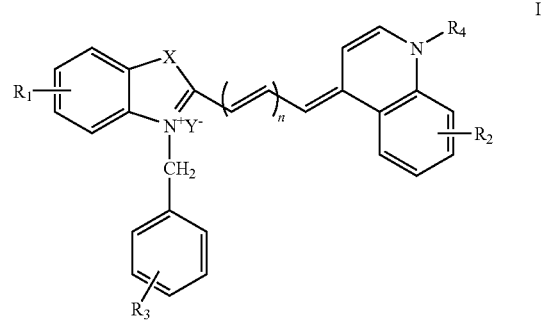

wherein
n is 1, 2 or 3;
X is $C(CH_3)_2$, O, S or Se;
$R_1$ and $R_2$ are each independently selected from H, $C_{1-18}$alkyl, —$C_{1-6}$alkyl-$OR_5$ or a halogen;
$R_3$ is H, $C_{1-18}$alkyl, $OR_5$, —$C_{1-6}$alkyl-$OR_5$, $COOR_5$, $NO_2$, CN or a halogen;
$R_4$ is $C_{1-18}$alkyl, —$C_{1-6}$alkyl-$OR_5$, benzyl or a halogen, wherein said benzyl is optionally substituted with a substituent selected from a halogen, hydroxyl, sulfhydryl, cyano, nitro, alkyl, aryl, alkyloxy, heterocyclyl, haloalkyl, amino, alkylamino, amido or carboxyl;
$R_5$ is H or $C_{1-18}$alkyl; and
$Y^-$ is an anion; or

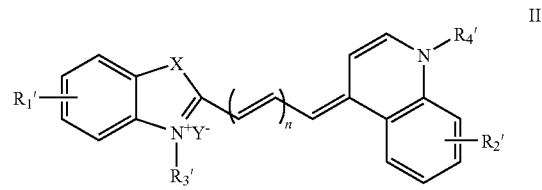

wherein
n is 1, 2 or 3;
X is $C(CH_3)_2$, O, S or Se;
$R_1'$ and $R_2'$ are each independently selected from H, OH, $C_{1-18}$alkyl, $C_{1-6}$alkylOR$_5'$, $C_{1-18}$alkylsulfonyl, phenyl or a halogen;
$R_3'$ and $R_4'$ are each independently selected from $C_{1-18}$alkylCOOR$_6'$, $C_{1-18}$alkylOR$_6'$ or benzyl, wherein said benzyl is optionally substituted with a substituent selected from a halogen, hydroxyl, sulfhydryl, cyano, nitro, alkyl, aryl, alkyloxy, heterocyclyl, haloalkyl, amino, alkylamino, amido or carboxyl, provided that $R_3'$ and $R_4'$ are not simultaneously benzyl, and $R_4'$ is not $C_{1-18}$alkyl$OR_6'$ when $R_3'$ is benzyl;

$R_5'$ is $C_{1-18}$alkyl or H;

$R_6'$ is $C_{1-18}$alkyl, H or phenyl, wherein said phenyl is optionally substituted with a substituent selected from a halogen, hydroxyl, sulfhydryl, cyano, nitro, alkyl, aryl, alkyloxy, heterocyclyl, haloalkyl, amino, alkylamino, amido or carboxyl; and Y— is an anion;

(2) Cationic surfactants that are quinolinium salt-type cationic surfactants having the following general formulae III and/or IV:

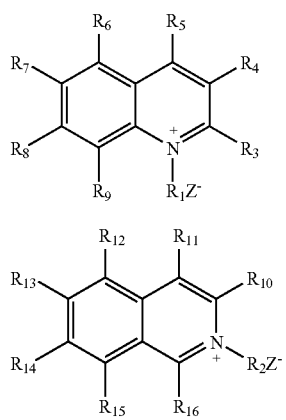

wherein $R_1$ and $R_2$ are each independently selected from $C_{6-18}$alkyl and $C_{6-18}$haloalkyl;

$R_3$ to $R_{16}$ are each independently selected from H, OH, $C_{1-4}$alkyl, $C_{1-4}$alkyloxy and sulphonyl; and $Z^-$ is a halogen ion; and/or quaternary ammonium salt-type cationic surfactants having the following general formula V:

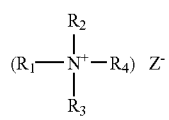

wherein $R_1$ is $C_{6-14}$alkyl or $C_{6-14}$alkenyl, and in one embodiment straight alkyls such as hexyl, octyl, decyl, lauryl or myristyl, and in another embodiment straight alkyls such as octyl, decyl, lauryl or myristyl;

$R_2$ is $C_{1-4}$alkyl or $C_{2-4}$alkenyl, for example, in one embodiment methyl, ethyl, propyl, butyl or butenyl, and in another embodiment methyl, ethyl or propyl;

$R_3$ is $C_{1-4}$alkyl or $C_{2-4}$alkenyl, for example, in one embodiment methyl, ethyl, propyl, butyl or butenyl, and in another embodiment methyl, ethyl or propyl;

$R_4$ is $C_{1-4}$alkyl, $C_{2-4}$alkenyl or benzyl, for example, in one embodiment methyl, ethyl, propyl, butyl, butenyl or benzyl, and in another embodiment methyl, ethyl or propyl;

$Z^-$ is a halogen ion;

(3) at least one nonionic surfactant; and (4) optionally at least one anionic compound selected from those having one or more carboxyl or sulphonyl groups.

In another aspect of the present disclosure there is provided a kit useful for differentiating and counting leukocytes, said kit comprising the reagent for differentiating and counting leukocytes according to any embodiment of the present disclosure, wherein said reagent can either be a reagent system comprising a single component or a reagent system comprising two or more reagent components.

In yet another aspect of the present disclosure there is provided a method for differentiating and counting leukocytes, said method comprising the following steps of: (1) adding and mixing a blood sample with the reagent according to any embodiment of the present disclosure or into the reagent comprised in the kit provided by the present disclosure and allowing the mixture to react for a period of time, so as to lyse the erythrocytes and the platelets, damage the leukocytes and bring about morphological changes to the respective leukocyte subtypes, and fluorescently label the nucleic acid substances in the leukocytes; and (2) differentiating and counting the leukocytes in the blood sample by detecting the fluorescent intensity information and scattered light intensity information of the leukocytes.

The reagent, kit and method disclosed in the present disclosure can identify leukocytes in blood samples into five subtypes in a very short time, or at least achieve the differentiation and counting of four leukocyte groupings, meanwhile immature and abnormal cells such as immature granulocyte and abnormal lymphocytes can be identified. Additionally, the results of differentiation can be achieved steadily under the reaction temperature of 20-50° C. Therefore, in practical usage, only a heating device may be needed to be installed in the detection apparatus and a refrigerating device may be omitted, which greatly reduces the apparatus cost. The use of the reagent and method disclosed in the present disclosure for differentiating leukocytes achieves a nevertheless good differentiation of leukocytes in the aged blood stored for two to three days in vitro, suffers from little influence by ambient temperature, and covers a wider range of application.

DEFINITIONS

Unless otherwise specified, the following terms as used herein have the following meanings.

The term "alkyl" as used herein individually or in combination with other groups refers to straight or branched alkyl groups containing 1-18 carbon atoms, such as 1-12, or alternatively 1-8, or 1-6 carbon atoms. Reference to a single straight alkyl such as "n-propyl" specifically means a straight alkyl group, while reference to a single branched alkyl such as "isopropyl" specifically means a branched alkyl group. For example, "$C_{1-6}$alkyl" includes $C_{1-4}$alkyl, $C_{1-3}$alkyl, methyl, ethyl, n-propyl, isopropyl and tert-butyl. The same rules also apply to other groups as used throughout the present specification.

The term "alkyloxy" as used herein refers to "alkyl" as defined above attached to the group —O—, wherein said "alkyl" contains 1-18 carbon atoms, such as 1-12, or alternatively 1-8, or 1-6 carbon atoms, such as methoxy, ethoxy and propoxy.

The term "halogen" as used herein includes fluorine, chlorine, bromine and iodine.

The term "benzyl" as used herein refers to —$CH_2$-Ph group. Modification of a benzyl group by the phrase "optionally substituted with" means that the benzyl group either can exist in an unsubstituted form, or can be substituted with a suitable substituent at any suitable position. Suitable substituents include, but are not limited to, a halogen, hydroxyl, sulfhydryl, cyano, nitro, alkyl, aryl, alkoxy, heterocyclyl, haloalkyl, amino, alkylamino, amido, carboxyl, etc., so long as the compounds finally formed have the properties as contemplated by the present disclosure. In one embodiment, the benzyl group is optionally substituted with a halogen, hydroxyl, sulfhydryl, cyano, nitro or amino.

The term "heterocyclyl" as used herein refers to a single ring system or a fused ring system comprising 3-14 ring members, such as 3-10, or alternatively 3-6 ring members, that contains one or more heteroatoms selected from nitrogen, oxygen and sulfur.

The term "aryl" as used herein refers to an aromatic group containing 4-20 carbon atoms, such as 5-10 carbon atoms, that conforms with the Hückel's 4n+2 rule.

As used herein, the term "identification" and grammatical variants thereof, such as "identify", "identified" and "identifying", mean that the five leukocyte subtypes (monocyte, lymphocyte, neutrophil, eosinophil and basophil) as well as immature cells and abnormal cells are distinguished from each other in terms of the differences in fluorescence and scattered light information.

As used herein, the term "differentiate and count" and grammatical variants thereof, such as "differentiating and counting" and "differentiation and counting", refer to taking advantage of the differences in fluorescence and scattered light information to at least differentiate leukocytes into the following four groupings: three groupings corresponding to monocyte, lymphocyte and eosinophil respectively and one grouping corresponding to neutrophil plus basophil, and count the cell number in each grouping.

The Reagent of the Present Disclosure

In one aspect of the present disclosure there is provided a reagent which enables the identification of leukocytes in blood samples into five subtypes or at least achieves the differentiation and counting of four leukocyte groupings. Said five subtypes of leukocytes refer to monocyte, lymphocyte, neutrophil, eosinophil and basophil; said differentiation and counting of four leukocyte groupings refers to differentiating leukocytes into the following four groupings: three groupings corresponding to monocyte, lymphocyte and eosinophil respectively and one grouping corresponding to neutrophil plus basophil, and counting the cell number in each grouping. In addition, the reagent of the present disclosure can also identify immature or abnormal cells which are rare in normal blood, including immature granulocytes, abnormal lymphocytes, heterotypic lymphocyte etc.

Said reagent comprises:

(1) Cationic cyanine compounds selected from those having the following general formulae I and II:

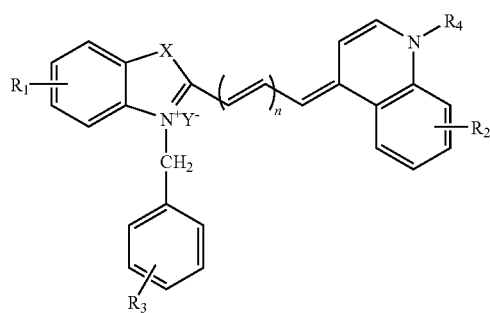

wherein
n is 1, 2 or 3;
X is $C(CH_3)_2$, O, S or Se;
$R_1$ and $R_2$ are each independently selected from H, $C_{1-18}$alkyl, —$C_{1-6}$alkyl-$OR_5$ or a halogen;
$R_3$ is H, $C_{1-18}$alkyl, $OR_5$, —$C_{1-6}$alkyl-$OR_5$, $COOR_5$, $NO_2$, CN or a halogen;
$R_4$ is $C_{1-18}$alkyl, —$C_{1-6}$alkyl-$OR_5$, benzyl or a halogen, wherein said benzyl is optionally substituted with a substituent selected from a halogen, hydroxyl, sulfhydryl, cyano, nitro, alkyl, aryl, alkyloxy, heterocyclyl, haloalkyl, amino, alkylamino, amido or carboxyl;
$R_5$ is H or $C_{1-18}$alkyl; and
$Y^-$ is an anion; or

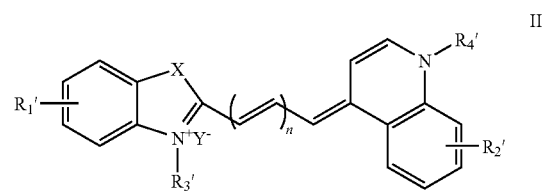

wherein
n is 1, 2 or 3;
X is $C(CH_3)_2$, O, S or Se;
$R_1'$ and $R_2'$ are each independently selected from H, OH, $C_{1-18}$alkyl, $C_{1-6}$ alkyl$OR_5'$, $C_{1-18}$alkylsulfonyl, phenyl or a halogen;
$R_3'$ and $R_4'$ are each independently selected from $C_{1-18}$alkyl$COOR_6'$, $C_{1-18}$alkyl$OR_6'$ or benzyl, wherein said benzyl is optionally substituted with a substituent selected from a halogen, hydroxyl, sulfhydryl, cyano, nitro, alkyl, aryl, alkyloxy, heterocyclyl, haloalkyl, amino, alkylamino, amido or carboxyl, provided that $R_3'$ and $R_4'$ are not simultaneously benzyl, and $R_4'$ is not $C_{1-18}$alkyl$OR_6'$ when $R_3'$ is benzyl;
$R_5'$ is $C_{1-18}$alkyl or H;
$R_6'$ is $C_{1-18}$alkyl, H or phenyl, wherein said phenyl is optionally substituted with a substituent selected from a halogen, hydroxyl, sulfhydryl, cyano, nitro, alkyl, aryl, alkyloxy, heterocyclyl, haloalkyl, amino, alkylamino, amido or carboxyl; and
$Y^-$ is an anion;

(2) Cationic surfactants that are quinolinium salt-type cationic surfactants having the following general formulae III and/or IV:

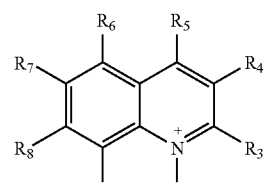

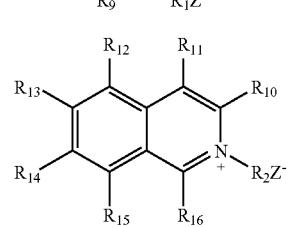

wherein $R_1$ and $R_2$ are each independently selected from $C_{6-18}$alkyl and $C_{6-18}$haloalkyl;

$R_3$ to $R_{16}$ are each independently selected from H, OH, $C_{1-4}$alkyl, $C_{1-4}$alkyloxy and sulphonyl; and $Z^-$ is a halogen ion; and/or quaternary ammonium salt-type cationic surfactants having the following general formula V:

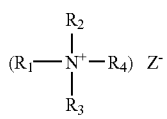

V wherein $R_1$ is $C_{6-14}$alkyl or $C_{6-14}$alkenyl, and in one embodiment straight alkyls such as hexyl, octyl, decyl, lauryl or myristyl, and in another embodiment straight alkyls such as octyl, decyl, lauryl or myristyl;

$R_2$ is $C_{1-4}$alkyl or $C_{2-4}$alkenyl, for example, in one embodiment methyl, ethyl, propyl, butyl or butenyl, and in another embodiment methyl, ethyl or propyl;

$R_3$ is $C_{1-4}$alkyl or $C_{2-4}$alkenyl, for example, in one embodiment methyl, ethyl, propyl, butyl or butenyl, and in another embodiment methyl, ethyl or propyl;

$R_4$ is $C_{1-4}$alkyl, $C_{2-4}$alkenyl or benzyl, for example, in one embodiment methyl, ethyl, propyl, butyl, butenyl or benzyl, and in another embodiment methyl, ethyl or propyl;

$Z^-$ is a halogen ion;

(3) at least one nonionic surfactant; and (4) optionally, at least one anionic compound selected from those having one or more carboxyl or sulphonyl groups.

1. Cationic Cyanine Compounds

The reagent of the present disclosure comprises at least one cationic cyanine compound. Cationic cyanine compounds are a kind of fluorescent dye that specifically binds to intracellular nucleic acid substances (including DNA, RNA and organelles with similar properties) and is excited to fluoresce, e.g., by red laser irradiation whose wavelength range is 633 nm to 650 nm. Different types of cells can be differentiated in terms of the differences in fluorescence intensities due to the variance in the amounts of intracellular nucleic acid substances, the detection signals for the fluorescence intensities being capable of amplification to aid differentiation.

The cationic cyanine compounds useful in the present disclosure are those having the following general formulae I or II:

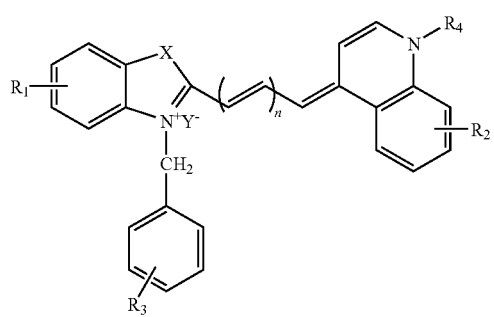

I wherein n is 1, 2 or 3;

X is $C(CH_3)_2$, O, S or Se;

$R_1$ and $R_2$ are each independently selected from H, $C_{1-18}$alkyl, —$C_{1-6}$alkyl-$OR_5$ or a halogen;

$R_3$ is H, $C_{1-18}$alkyl, $OR_5$, —$C_{1-6}$alkyl-$OR_5$, $COOR_5$, $NO_2$, CN or a halogen;

$R_4$ is $C_{1-18}$alkyl, —$C_{1-6}$alkyl-$OR_5$, benzyl or a halogen, wherein said benzyl is optionally substituted with a substituent selected from a halogen, hydroxyl, sulfhydryl, cyano, nitro, alkyl, aryl, alkyloxy, heterocyclyl, haloalkyl, amino, alkylamino, amido or carboxyl;

$R_5$ is H or $C_{1-18}$alkyl; and $Y^-$ is an anion.

In one embodiment, n is 1 or 2. In another embodiment, n is 1.

In one embodiment, X is $C(CH_3)_2$, O or S. In another embodiment, X is $C(CH_3)_2$ or S. In a further embodiment X is S.

In one embodiment, $R_1$ and $R_2$ are each independently selected from H, $C_{1-18}$alkyl or a halogen. In another embodiment, $R_1$ and $R_2$ are each independently selected from H or $C_{1-18}$alkyl. In still another embodiment, $R_1$ and $R_2$ are each independently selected from H or $C_{1-12}$alkyl. In yet another embodiment, $R_1$ and $R_2$ are each independently selected from H or $C_{1-6}$alkyl. In a further embodiment, $R_1$ and $R_2$ are both H.

In one embodiment, $R_3$ is H, $C_{1-18}$alkyl, $OR_5$, $COOR_5$ or a halogen, and in another embodiment, $R_3$ is H, $C_{1-12}$alkyl, $OR_5$, $COOR_5$ or a halogen. In a further embodiment, $R_3$ is H, $C_{1-6}$alkyl, $OR_5$, $COOR_5$ or a halogen.

In one embodiment, $R_4$ is $C_{1-18}$alkyl, benzyl or a halogen, wherein said benzyl is optionally substituted with a substituent selected from a halogen, hydroxyl, sulfhydryl, cyano, nitro, alkyl, aryl, alkyloxy, heterocyclyl, haloalkyl, amino, alkylamino, amido or carboxyl, and in another embodiment, $R_4$ is $C_{1-18}$alkyl or benzyl, wherein said benzyl is optionally substituted with a substituent selected from a halogen, hydroxyl, sulfhydryl, cyano, nitro or amino. In still another embodiment, $R_4$ is $C_{1-12}$alkyl or benzyl, wherein said benzyl is optionally substituted with a substituent selected from a halogen, hydroxyl, sulfhydryl, cyano, nitro or amino. In a further embodiment, $R_4$ is $C_{1-6}$alkyl or benzyl, wherein said benzyl is optionally substituted with a substituent selected from a halogen, hydroxyl, sulfhydryl, cyano, nitro or amino.

In one embodiment, $R_5$ is H or $C_{1-12}$alkyl. In another embodiment, $R_5$ is H or $C_{1-6}$alkyl.

In one embodiment, $Y^-$ is a halogen ion, $ClO_4^-$, $PF_6^-$, $CF_3SO_3^-$, $BF_4^-$, acetate or p-toluenesulfonate anion.

In one embodiment, the aforesaid compounds having the general formula I are the following Compound A, Compound B or Compound C:

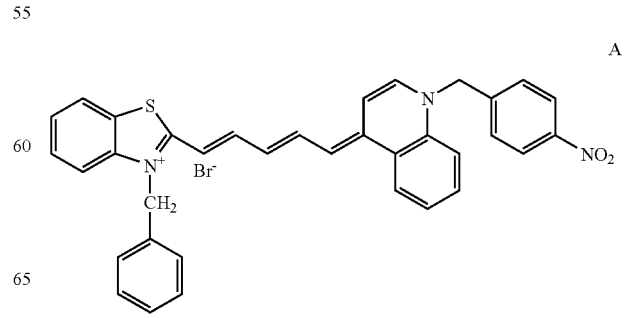

A

-continued

B

[Structure B: benzothiazole-quinoline cyanine dye with N-benzyl (4-methoxybenzyl) group, I⁻ counterion]

C

[Structure C: benzothiazole-quinoline cyanine dye with N-benzyl groups, Br⁻ counterion]

The compounds having the general formula I and method of preparation thereof have been disclosed in Chinese patent application No. 200710137258.6, which is incorporated herein by reference in its entirety.

II

[Structure II: general formula showing benzothiazole-quinoline cyanine with substituents $R_1'$, $R_2'$, $R_3'$, $R_4'$, X, n, $Y^-$]

wherein
n is 1, 2 or 3;
X is $C(CH_3)_2$, O, S or Se;
$R_1'$ and $R_2'$ are each independently selected from H, OH, $C_{1-18}$alkyl, $C_{1-6}$alkylOR$_5'$, $C_{1-18}$alkylsulfonyl, phenyl or a halogen;
$R_3'$ and $R_4'$ are each independently selected from $C_{1-18}$alkylCOOR$_6'$, $C_{1-18}$alkylOR$_6'$ or benzyl, wherein said benzyl is optionally substituted with a substituent selected from a halogen, hydroxyl, sulfhydryl, cyano, nitro, alkyl, aryl, alkyloxy, heterocyclyl, haloalkyl, amino, alkylamino, amido or carboxyl, provided that $R_3'$ and $R_4'$ are not simultaneously benzyl, and $R_4'$ is not $C_{1-18}$alkylOR$_6'$ when $R_3'$ is benzyl;
$R_5'$ is $C_{1-18}$alkyl or H;
$R_6'$ is $C_{1-18}$alkyl, H or phenyl, wherein said phenyl is optionally substituted with a substituent selected from a halogen, hydroxyl, sulfhydryl, cyano, nitro, alkyl, aryl, alkyloxy, heterocyclyl, haloalkyl, amino, alkylamino, amido or carboxyl; and
$Y^-$ is an anion.

In one embodiment, n is 1 or 2. In another embodiment, n is 1.

In one embodiment, X is $C(CH_3)_2$, O or S. In another embodiment, X is $C(CH_3)_2$ or S. In a further embodiment, X is S.

In one embodiment, $R_1'$ and $R_2'$ are each independently selected from H or $C_{1-18}$alkyl. In another embodiment, $R_1'$ and $R_2'$ are each independently selected from H or $C_{1-6}$alkyl. In a further embodiment, $R_1'$ and $R_2'$ are both H.

In one embodiment, $R_3'$ and $R_4'$ are each independently selected from $C_{1-8}$alkylCOOR$_6'$, $C_{1-8}$alkylOR$_6'$ or benzyl, wherein said benzyl is optionally substituted with a substituent selected from a halogen, hydroxyl, sulfhydryl, cyano, nitro or amino. In another embodiment, $R_3'$ and $R_4'$ are each independently selected from $C_{1-6}$alkylCOOR$_6'$, $C_{1-6}$alkylOR$_6'$ or benzyl, wherein said benzyl is optionally substituted with a substituent selected from a halogen, hydroxyl, sulfhydryl, cyano, nitro or amino.

In one embodiment, $R_5'$ is H or $C_{1-12}$alkyl. In another embodiment, $R_5'$ is H or $C_{1-6}$alkyl.

In one embodiment, $R_6'$ is $C_{1-6}$alkyl or phenyl, wherein said phenyl is optionally substituted with a substituent selected from a halogen, hydroxyl, sulfhydryl, cyano, nitro, alkyl, aryl, alkyloxy, heterocyclyl, haloalkyl, amino, alkylamino, amido or carboxyl.

$Y^-$ is an anion, which can be any suitable anion, including but not limited to an inorganic anion or an organic anion, for example a halogen ion, $ClO_4^-$, $PF_6^-$, $CF_3SO_3^-$, $BF_4^-$, acetate or p-toluenesulfonate anion.

In one embodiment, the aforesaid compounds having the general formula II are the following Compound D, Compound E or Compound F:

D

[Structure D: benzothiazole-quinoline cyanine dye with N-benzyl group and N-(hexyl ethyl ester) chain, Br⁻ counterion]

E

[Structure E: benzothiazole-quinoline cyanine dye with N-hydroxyethyl and N-(propyl ethyl ester) chain, Br⁻ counterion]

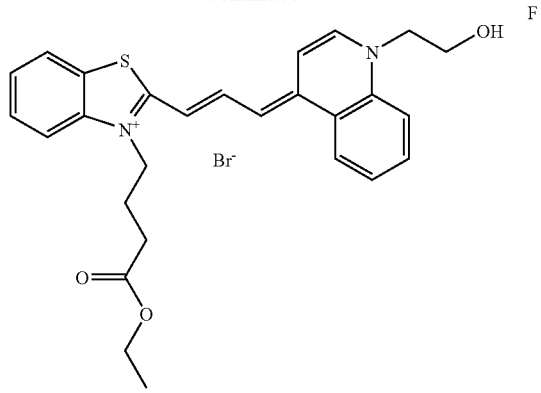

F

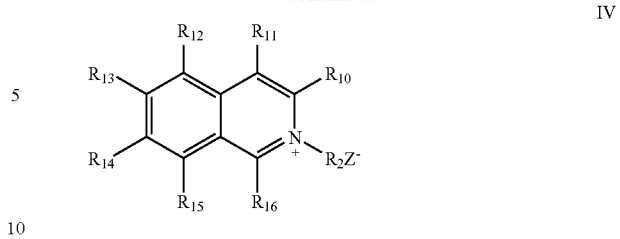

IV

The compounds having the general formula II and method of preparation thereof have been disclosed in Chinese patent application No. 200810002503.7, which is incorporated herein by reference in its entirety.

The compounds disclosed herein can be directly used for staining biological samples in the form of salts as described herein. Alternatively, in one embodiment, the compounds disclosed herein can exist in the form of derivatives of the compounds of the general formula I or II, said derivatives including, but not limited to, conjugates.

Typically, conjugates are used in the fluorescence activated cell sorter (FACS). "Conjugates" as used herein refer to the compounds formed by attaching the compounds disclosed herein to other molecules via covalent bonds. Molecules that can be conjugated with the compounds disclosed herein may be those that specifically bind to cells or cell components, including, but not limited to, antibodies, antigens, receptors, ligands, enzymes, substrates, coenzymes or the like.

In various embodiments of the present disclosure, the above compounds are used in a suitable concentration in the range of 0.002 ppm to 2000 ppm, such as in the range of 0.02 ppm to 200 ppm, e.g. in the range of 0.2 ppm to 20 ppm.

As the above compounds are more stable in non-aqueous solvents, desirably they are stored separate from the water soluble components of the reagent disclosed in the present disclosure. The term "water soluble components" as used herein refer to the cationic surfactants, nonionic surfactants and anionic compounds comprised in the reagent of the present disclosure.

2. Cationic Surfactants

The reagent of the present disclosure may comprise cationic surfactants. They primarily function as a hemolytic agent to lyse erythrocytes and platelets and partly damage the cell membrane of leukocytes so that the dye can rapidly enter the leukocytes and bind with intracellular nucleic acid substances.

Said cationic surfactants may include quinolinium salt-type cationic surfactants having the following general formulae III and/or IV:

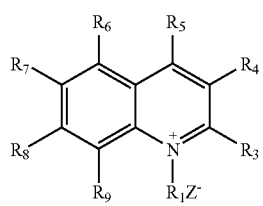

III wherein
$R_1$ and $R_2$ are each independently selected from $C_{6-18}$alkyl and $C_{6-18}$haloalkyl;
$R_3$ to $R_{16}$ are each independently selected from H, OH, $C_{1-4}$alkyl, $C_{1-4}$alkyloxy and sulphonyl
$Z^-$ is a halogen ion;
and may additionally include or alternatively include
quaternary ammonium salt-type cationic surfactants having the following general formula V:

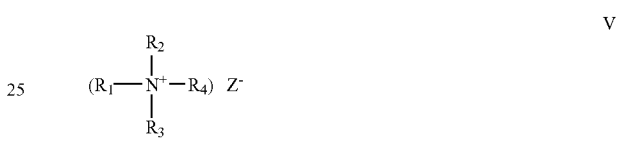

V wherein
$R_1$ is $C_{6-14}$alkyl or $C_{6-14}$alkenyl, and in one embodiment straight alkyls such as hexyl, octyl, decyl, lauryl or myristyl, and in another embodiment straight alkyls such as octyl, decyl, lauryl or myristyl;
$R_2$ is $C_{1-4}$alkyl or $C_{2-4}$alkenyl, for example, in one embodiment methyl, ethyl, propyl, butyl or butenyl, and in another embodiment methyl, ethyl or propyl;
$R_3$ is $C_{1-4}$alkyl or $C_{2-4}$alkenyl, for example, in one embodiment methyl, ethyl, propyl, butyl or butenyl, and in another embodiment methyl, ethyl or propyl;
$R_4$ is $C_{1-4}$alkyl, $C_{2-4}$alkenyl or benzyl, for example, in one embodiment methyl, ethyl, propyl, butyl, butenyl or benzyl, and in another embodiment methyl, ethyl or propyl;
$Z^-$ is a halogen ion.

Exemplary quinolinium salt-type cationic surfactants useful in the present disclosure are selected from octylquinolinium bromide, octylisoquinolinium bromide, decylquinolinium bromide, decylisoquinolinium bromide, laurylquinolinium bromide, laurylisoquinolinium bromide, myristylquinolinium bromide, myristylisoquinolinium bromide, cetylisoquinolinium bromide and combinations thereof.

Exemplary quaternary ammonium salt-type cationic surfactants useful in the present disclosure are selected from octyltrimethyl ammonium chloride, octyltrimethyl ammonium bromide, decyltrimethyl ammonium chloride, decyltrimethyl ammonium bromide, lauryltrimethyl ammonium chloride, lauryltrimethyl ammonium bromide, myristyltrimethyl ammonium chloride, myristyltrimethyl ammonium bromide, and combinations thereof.

The above cationic surfactants can be used in a concentration in the range of 0.1 g/L to 5.0 g/L depending on the identity of the substance used. The hemolytic capability of the above cationic surfactants is positively correlated to the chain length of $R_1$ in the general formula III, $R_2$ in the general formula IV and $R_1$ in the general formula V. The more the number of carbon atoms in the chain, the higher the hemolytic capability, and the lower the concentration needed. The optimal concentration used in the present disclosure for the cationic surfactants is one having a corresponding hemolytic capability that allows the complete lysis of erythrocytes and platelets into cell debris and partial damage of the cell membrane of leukocytes so that the dye can fully enter the leukocytes. The concentration used is better far lower than an amount for lysing cell membrane so as to make leukocyte nucleus naked.

3. Nonionic Surfactants

The reagent of the present disclosure may comprise at least one nonionic surfactant which is useful to damage the leukocytes and induce pyknosis of intracellular substances so that the differences in the scattered light intensities from the intracellular structures of different leukocyte subtypes are magnified. Said nonionic surfactants may be selected from the polyoxyethylene-type nonionic surfactants having the following general formula VI or combinations thereof.

$$R_1-R_2-(CH_2CH_2O)_n-H \quad VI$$

wherein $R_1$ is $C_{8-23}$alkyl or $C_{8-23}$alkenyl, for example, in one embodiment $R_1$ is a straight alkyl, such as octyl, decyl, lauryl, myristyl, cetyl or stearyl, and in another embodiment $R_1$ is a straight alkyl, such as lauryl, myristyl or cetyl;

$R_2$ is —O—,

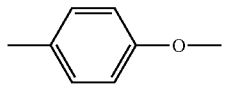

or —COO—;

n is an integer of 8-30.

In one embodiment, said nonionic surfactants can be selected from polyoxyethylene (23) lauryl ether, polyoxyethylene (25) cetyl ether, polyoxyethylene (30) cetyl ether, and combinations thereof.

The concentration of said polyoxyethylene-type nonionic surfactants can vary in a large range, e.g. from 0.5 g/L to 5 g/L, depending on the identity of the substance used. The ability of the aforesaid polyoxyethylene-type nonionic surfactants to damage cells is correlated with the chain length of $R_1$ and $R_2$ in the general formula VI, as well as the polymerization number (n) of polyoxyethylene. Specifically, given a certain polymerization number (n) of polyoxyethylene, the more the number of carbon atoms in the hydrophobic groups represented by $R_1$ and $R_2$, the weaker the ability to damage cells, the higher the concentration needed; and given a certain number of carbon atoms in the hydrophobic groups represented by $R_1$ and $R_2$, the more the polymerization number (n) of polyoxyethylene, the weaker the ability to damage cells, the higher the concentration needed.

The nonionic surfactants contained in the reagent of the present disclosure can either be one nonionic surfactant or the combination of two or more nonionic surfactants. As different nonionic surfactants have varied ability to damage the respective leukocyte subtypes, the use of two or more nonionic surfactants in combination will have a more obvious effect on the differentiation of leukocyte subtypes in blood samples. If two or more nonionic surfactants are used in combination, the concentration for each of the nonionic surfactants is in the range described above for a single nonionic surfactant while an optimal synergistic effect is attained.

4. An Anionic Compound Selected from Those Having One or More Carboxyl or Sulphonyl Groups The reagent of the present disclosure optionally comprises at least one anionic compound which is useful to bind with intracellular cations so that the scattered light intensities from inside the cells of the leukocyte subtypes are changed. Said anionic compounds are selected from acids having carboxyl or sulphonyl groups and salts thereof.

Said anionic compounds can be carboxylic acids having one or more carboxyl groups and salts thereof. In the case of carboxylic acids having one carboxyl group and salts thereof, they may be selected, among others, from formic acid and alkali metal salts thereof, acetic acid and alkali metal salts thereof, or benzoic acid and alkali metal salts thereof, while in the case of carboxylic acids having more carboxyl groups and salts thereof, they may be selected, among others, from citric acid and alkali metal salts thereof, malic acid and alkali metal salts thereof, or orthophthalic acid and alkali metal salts thereof.

Said anionic compounds may also be sulfo group-bearing sulphonic acid and salts thereof. In one embodiment, they are selected from benzenesulphonic acid and alkali metal salts thereof, α-naphthalenesulphonic acid and alkali metal salts thereof, or taurine etc.

The concentration for the aforesaid anionic compounds is optimally such that the leukocyte subtypes are distinguished from each other desirably in terms of scattered light intensities, said concentration being suitably in the range of 0.1 g/L to 20 g/L, such as 1 g/L to 5 g/L, and being adjustable as appropriate depending on the identity of the substance used.

5. Alcohol Compounds

The reagent of the present disclosure optionally comprises alcohol compounds. Without being bound by any theory, the presence of alcohol compounds helps to induce pyknosis of the intracellular proteinaceous substances, prevent excess drain of cytoplasm, protect the cell membrane of leukocytes from excess damage by the hemolytic agent and maintain a definite morphology and internal structure of the leukocytes. This is particularly helpful to keep stable the intracellular proteinaceous substances of leukocytes in the aged blood so that the scattered light intensities are maintained and the differentiation result of leukocytes in the aged blood is guaranteed. The identity of the alcohols is not particularly limited and they can be alkyl alcohols such as methanol, ethanol, isopropanol and n-butanol, and aromatic alcohols such as benzyl alcohol and 2-phenoxyethanol.

It is believed that when a blood sample is taken from the body, the blood cells inside it continue to metabolize, consuming the oxygen in the sample and generating acidic metabolic products such as lactic acid. However, as such metabolism occurs in vitro, the cells are unable to divide and regenerate, therefore the metabolism of the intracellular proteins and nucleic acids tends to become unbalanced over time and the cells age gradually. For the same blood sample, the aged blood differs from the fresh blood by certain changes in the morphology and internal structure of the leukocyte subtypes. This is not much of a problem when the reagent of the present disclosure is used. Treatment of the somewhat aged blood by the reagent containing alcohols in a certain concentration range renders the blood as if it were fresh blood, so that the difference in the differentiation of the respective leukocyte subtypes between the aged blood and the fresh blood is in an acceptable range. Thus, when a retest is required in clinical, the leukocytes can still be differentiated and counted correctly. While the specific mechanism is unknown, it is presumed that alcohols function to denature proteins so that the vulnerable cell membrane and intracellular proteinaceous substances of the aged blood cells are fixed to such an extent that the excess damage of the cells by such component of hemolytic agent as cationic surfactant is inhibited, making the differentiation result of the aged blood similar to that of the fresh blood.

The concentration of the alcohol compounds, which can vary in a large range of 0.1 g/L-200 g/L, decreases as the number of carbon atoms in the structure of the compounds increases.

6. Other Components

The reagent of the present disclosure may also comprise buffering agents to maintain the pH of the reagent at around 6 to 8. The choice of buffering agents is not particularly limited, and the common buffering systems such as phosphate buffer, borate buffer, tris(hydroxymethyl)aminomethane hydrochloride (Tris) buffer, and 4-(2-Hydroxyethyl)-1-piperazineethanesulfonic acid (HEPES) can be used in the present disclosure. The buffering agents are normally used in an amount in the range of 10-500 mM.

The reagent of the present disclosure may further comprise other conventional additives such as preserving agents and metal chelating agents to contribute to antisepsis and prolonged storage of the reagent. The identity of the preserving agents is not particularly limited, and commercially available preserving agents such as Kathon and gentamicin can be used; while ethylendiamine tetraacetic acid and its alkali metal salts can be chosen as the metal chelating agents. The concentrations of these additives are desirably such that the differentiation and counting of leukocytes are not influenced.

The osmotic pressure of the reagent of the present disclosure is desirably in the range of 10 mOsm to 100 mOsm. Use of such a relatively lower osmotic pressure facilitates the lysis of erythrocytes and platelets and therefore relatively smaller amounts of the components of the hemolytic agent are required.

Kit for Differentiating and Counting Leukocytes

In still another aspect of the present disclosure there is provided a kit useful for differentiating and counting leukocytes, said kit comprising the reagent of the present disclosure. Said kit can be used to treat blood samples and enables the identification of leukocytes into five subtypes or at least achieve the differentiation and counting of four leukocyte groupings.

Said reagent included in said kit can either be a reagent system comprising a single component or a reagent system comprising two or more reagent components.

As the cationic cyanine compounds in the reagent disclosed in the present disclosure are typically more stable in non-aqueous solvents, they may be stored separate from the water soluble component of the reagent disclosed in the present disclosure. In one embodiment, said cationic cyanine compounds are stored in organic solvents. There are no particular limitations on the identity of organic solvents, so long as they can fully dissolve said cationic cyanine compounds and are somewhat soluble in water, and the common organic solvents such as methanol, ethanol, glycol, glycerol and dimethylsulfoxide can be used.

The concentration of said cyanine compounds stored in organic solvents is such that the full dissolution of the compounds is ensured and that it is not lower than the final use concentration of the compounds. Generally, said cyanine compounds are desirably stored in organic solvents in a concentration in the range of 0.01 ppm to 1000 ppm, such as in the range of 1 ppm to 100 ppm.

In the present disclosure, said water soluble component is also referred to as "hemolytic agent" and the component comprising said cationic cyanine compounds referred to as "dyeing liquid." When the kit disclosed in the present disclosure is used, the dyeing liquid and the hemolytic agent are mixed with the blood sample in a certain volume ratio for a period of time prior to conducting detection. The volume ratio of said dyeing liquid to said hemolytic agent is not particularly limited, and they are generally mixed in a volume ratio of 1:10 to 1:100, such as 1:40 to 1:60.

Method for Differentiating and Counting Leukocytes

In yet another aspect of the present disclosure there is provided a method for differentiating and counting leukocytes, said method comprising the following steps:

1. Adding and mixing a blood sample with the reagent disclosed in the present disclosure and allowing the mixture to react for a period of time, so as to lyse the erythrocytes and the platelets, damage the leukocytes and bring about morphological changes among the respective leukocyte subtypes, and fluorescently label the nucleic acid substances in the leukocytes; and 2. Identifying the leukocytes in the blood sample into five subtypes, i.e. lymphocyte, monocyte, neutrophil, eosinophil and basophil by detecting the fluorescent intensity information and scattered light intensity information of the various leukocytes; or at least differentiating the leukocytes into the following four groupings: three groupings corresponding to monocyte, lymphocyte and eosinophil respectively and one grouping corresponding to neutrophil plus basophil, and counting the cell number in each grouping; delimiting certain areas in the scattergram formed by plotting the fluorescence intensities against scattered light intensities as the identification areas for immature cells such as immature granulocyte or abnormal cells such as abnormal lymphocytes, so that these immature granulocytes or abnormal cells are identified.

The reaction time for the mixture may be in the range of 5-30 seconds, such as 15-25 seconds. As the reagent disclosed in the present disclosure can quickly act on leukocytes to partially damage their cell membrane, the dye can rapidly penetrate the cell membrane to label the intracellular nucleic acid substances. Therefore the method disclosed in the present disclosure enables rapid differentiation and counting of leukocytes, allows for a faster speed of detection using automatic detection devices, and is especially suitable for the detection of a large number of blood samples.

There is no particular limitation on the mixing ratio of the blood sample to the reagent disclosed in the present disclosure during the process of differentiation as described in the present disclosure. Normally, the mixing ratio of the blood sample to the reagent disclosed in the present disclosure is in the range of 1:10 to 1:100 by volume, such as 1:40 to 1:60 by volume.

The reaction temperature for the process of differentiation as described in the present disclosure may be a broad range of 20° C. to 50° C., said range having been experimentally demonstrated to permit a good differentiation of leukocytes by the reagent and method disclosed in the present disclosure, meaning that a stable differentiation result can be obtained with the reaction temperature set at any temperature point in the range of 20° C. to 50° C. Nevertheless, in one embodiment the reaction temperature as described in the present disclosure is in the range of 40° C. to 45° C., because the room temperature normally would not be higher than 40° C., so that in practical usage only a heating device is needed to be installed in the detection apparatus and a refrigerating device is omitted, which greatly reduces the apparatus cost.

The fluorescence intensity information as described in the present disclosure can be measured by using the laser flow cytometry method to detect side fluorescence at the detection angle of 90°; and intracellular morphological information can be measured by using the laser flow cytometry method to detect scattered light at the detection angle of 90°. The laser flow cytometry method as employed in the present disclosure can be performed on the publicly known device as shown in FIG. 1, wherein the laser light source can be selected to be that which conforms to the excitation wavelength of the fluorescent dye used.

In one embodiment, the method disclosed in the present disclosure involves the following steps of:

1. Adding a blood sample into the reagent disclosed in the present disclosure, so as to lyse the erythrocytes and the platelets, damage the leukocytes and bring about changes in morphology and internal structure among the respective leukocyte subtypes, and fluorescently label the nucleic acid substances in the leukocytes, so that sample fluids for detection are formed.

2. Ensheathing the sample fluids with sheath fluid, arranging them in a single line and passing them sequentially through the optoelectronic detection area in the flow chamber for laser irradiation, and then collecting the scattered light intensity information and the side fluorescence intensity information of the cells under irradiation by laser beams.

3. Analyzing the scattered light intensity information and the side fluorescence intensity information. In terms of the differences in the intensities of scattered light and fluorescence from the respective leukocyte subtypes, leukocytes can be differentiated and counted in the 2-dimensional or 3-dimensional scattergram formed by plotting the side fluorescence intensity against the scattered light intensity and the immature cells or abnormal cells can also be identified. The scattered light intensity information includes side-scattered light intensity information or forward scattered light intensity information, so the differentiation of leukocyte subtypes can be achieved in a 3-dimensional scattergram formed by plotting side fluorescence information against side-scattered light intensity information and forward scattered light intensity information, or in a 2-dimensional scattergram formed by plotting side fluorescence information against side-scattered light intensity information or forward scattered light intensity information.

Figure 3:
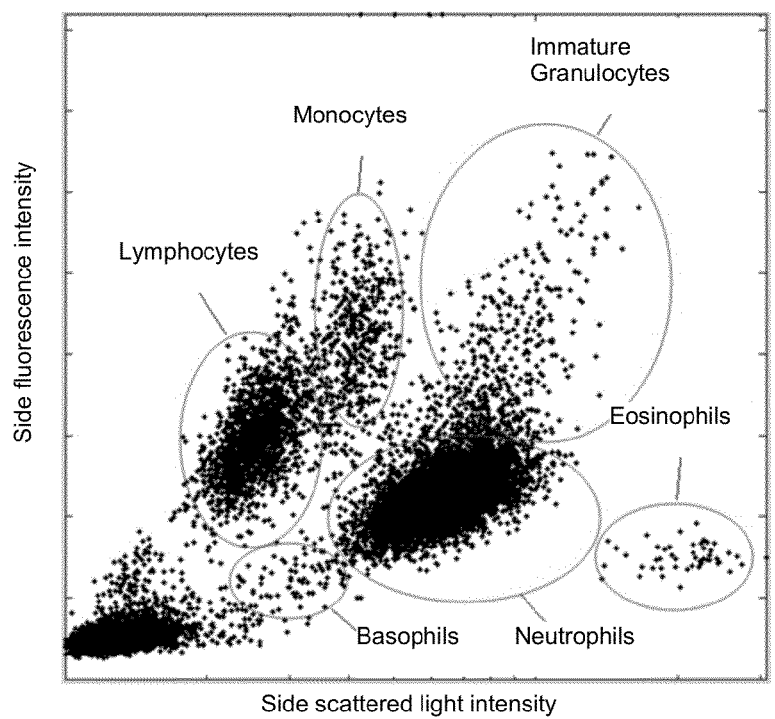
FIG. 3 is a scattergram formed by plotting the side fluorescence intensity against side-scattered light intensity of blood measured using the reagent for differentiating and counting leukocytes according to one embodiment as described in Example 2.
Figure 7:
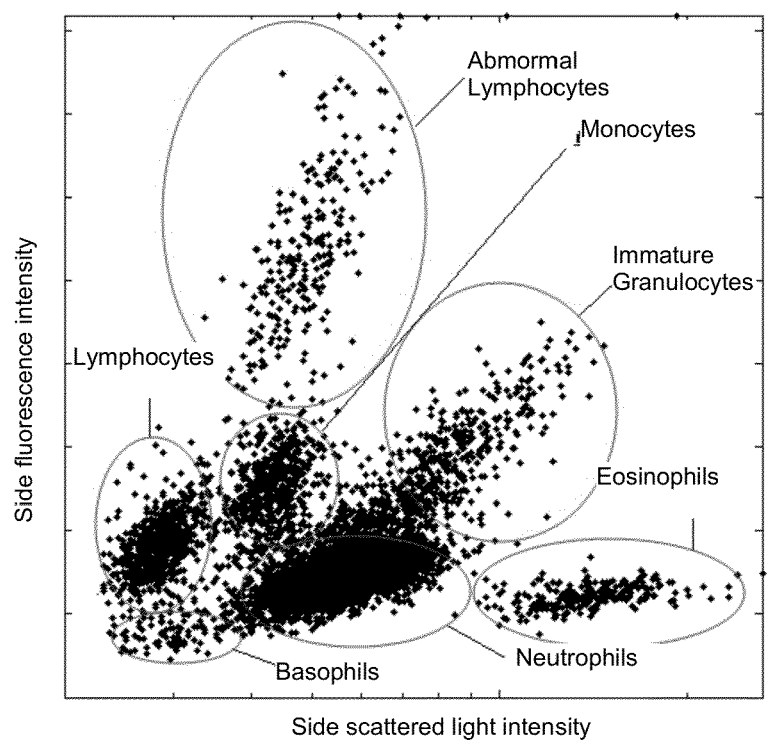
FIG. 7 is a scattergram formed by plotting the side fluorescence intensity against side-scattered light intensity of blood measured using the reagent for differentiating and counting leukocytes according to one embodiment as described in Example 6.

When the method disclosed in the present disclosure is used to differentiate and count leukocytes, immature granulocytes can be distinguished from those mature granulocytes, as well as abnormal lymphocytes also can be distinguished from those normal lymphocytes. The immature granulocytes are granulocytes at the early developmental stage, with large nucleus and plentiful intracellular nucleic acid substances. As such, in contrast to the mature granulocytes, the immature granulocytes bind more fluorescent dye and exhibit a stronger fluorescence excitation, so that they are markedly different from the mature granulocytes in terms of side fluorescence intensity, as shown in FIG. 3. And as exhibited in FIG. 4, the abnormal lymphocytes also show an obvious distinction from the normal lymphocytes in terms of side fluorescence intensity because they contain more nucleic acid substances. Moreover, the immature granulocytes and the abnormal lymphocytes can be indentified at the same test, as shown in FIG. 7.

EXAMPLES

The present disclosure is further illustrated by the following particular examples to which or by which the present disclosure is not limited, as is appreciated by one skilled in the art.

Unless otherwise stated, the detection apparatus for detecting blood cells is the BC series flow cytometer manufactured by Shenzhen Mindray Bio-Medical Electronics Co. Ltd (Shenzhen, People's Republic of China), with the detection wavelength being 640 nm. The schematic diagram of the optical system of the cell analyzer is as shown in FIG. 1.

Example 1

Reagent A for differentiating and counting leukocytes was formulated with the following ingredients:

| | |
|---|---:|
| The compound of the above structural formula A | 0.5 ppm |
| decylisoquinolinium bromide | 0.4 g/L |
| polyoxyethylene (23) lauryl ether | 1.3 g/L |
| sodium benzoate | 2.0 g/L |
| methanol | 50 g/L |
| monobasic sodium phosphate | 3 g/L |
| dibasic sodium phosphate | 4.8 g/L |

Figure 2:
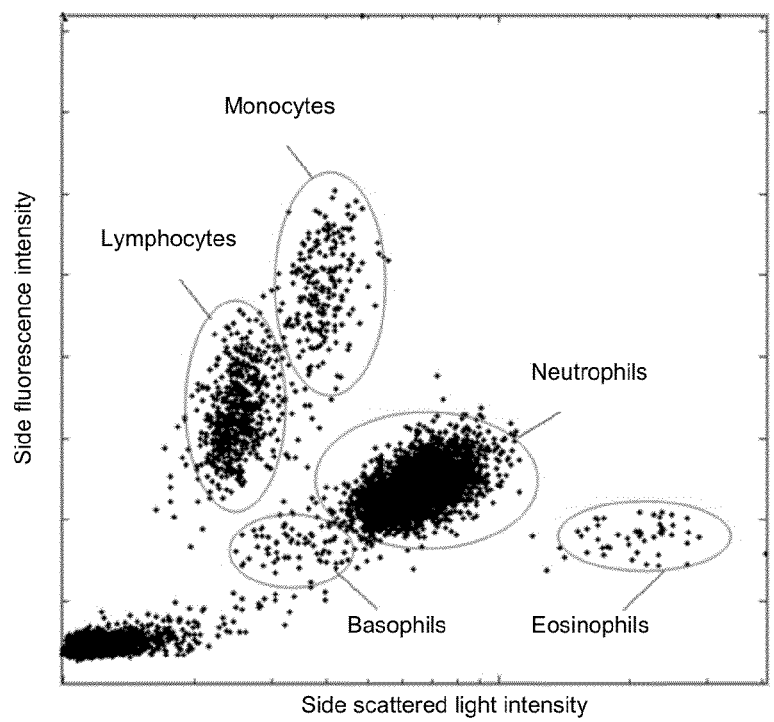
FIG. 2 is a scattergram showing the relationship between the side fluorescence intensity and the side-scattered light intensity when leukocytes are differentiated and counted according to the method of one embodiment as described in Example 1.

20 μl of fresh anti-coagulation blood sample was added into 1 ml of the aforesaid Reagent A, mixed for 25 seconds while the temperature was kept at 25° C., then leukocytes were detected using the laser flow cytometry method (light source: red semiconductor laser, wavelength 640 nm). Side fluorescence at the detection angle of 90° was used to detect the fluorescence intensity information of the leukocytes, and side-scattered light at the detection angle of 90° was used to detect the side-scattered light intensity information of the leukocytes. The result is as shown in FIG. 2, in which leukocytes are differentiated into five subtypes: lymphocyte, monocyte, neutrophil, eosinophil and basophil.

Example 2

Reagent B for differentiating and counting leukocytes was formulated with the following ingredients:

| | |
|---|---:|
| The compound of the above structural formula B | 0.5 ppm |
| myristylquinolinium bromide | 0.1 g/L |
| polyoxyethylene (25) cetyl ether | 1.5 g/L |
| benzenesulfonic acid | 2.0 g/L |
| Tris | 1.2 g/L | the pH being adjusted to 7.0 with hydrochloric acid.

20 μl of fresh anti-coagulation blood sample having a relatively higher percentage of immature granulocytes (IG) (the IG % was 2.5% as detected by microscopic examination) was added into 1 ml of the aforesaid Reagent B, mixed for 15 seconds while the temperature was kept at 45° C., then leukocytes were detected using the laser flow cytometry method (light source: red semiconductor laser, wavelength 640 nm). Side fluorescence at the detection angle of 90° was used to detect the fluorescence intensity information of the leukocytes, and side-scattered light at the detection angle of 90° was used to detect the side-scattered light intensity information of the leukocytes. The result is as shown in FIG. 3, a 2-dimensional scattergram formed by plotting fluorescence intensity against side-scattered light intensity, from which it can be seen that besides the normal lymphocytes, monocytes, neutrophils, basophils and eosinophils, there exhibits an obvious occurrence of immature granulocytes above the normal neutrophils. Calculated by manual delimitation of the immature granulocyte population in the scattergram, the IG % is 2.3%, which is close to the percentage detected by microscopic examination.

Example 3

Reagent C for differentiating and counting leukocytes was formulated with the following ingredients:

| | |
|---|---|
| The compound of the above structural formula C | 0.5 ppm |
| lauryltrimethyl ammonium chloride | 0.6 g/L |
| polyoxyethylene (30) cetyl ether | 1.6 g/L |
| taurine | 2.0 g/L |
| Tris | 1.2 g/L | the pH being adjusted to 7.0 with hydrochloric acid.

Figure 4:
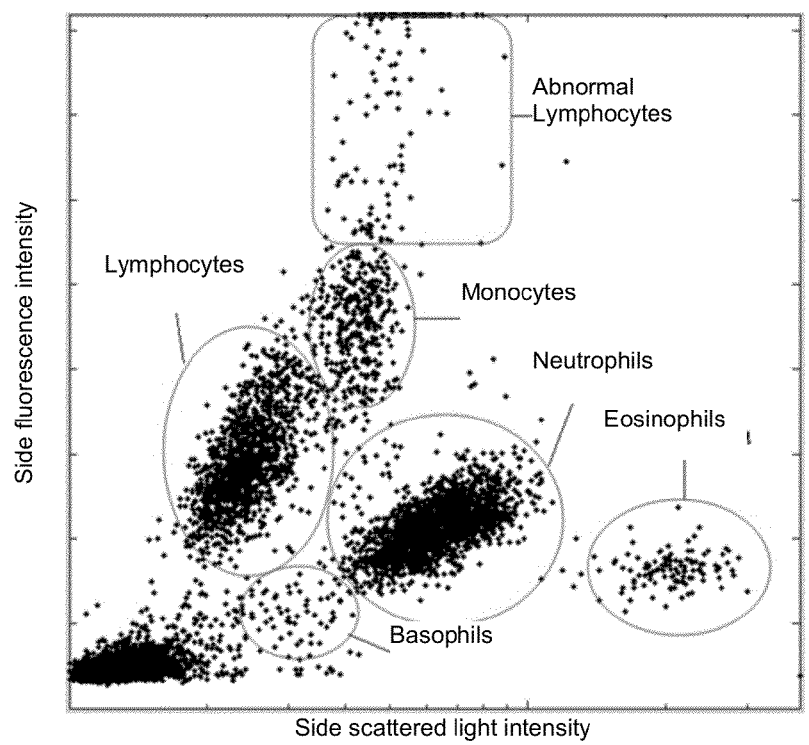
FIG. 4 is a scattergram formed by plotting the side fluorescence intensity against side-scattered light intensity of blood measured using the reagent for differentiating and counting leukocytes according to one embodiment as described in Example 3.
Figure 5A:
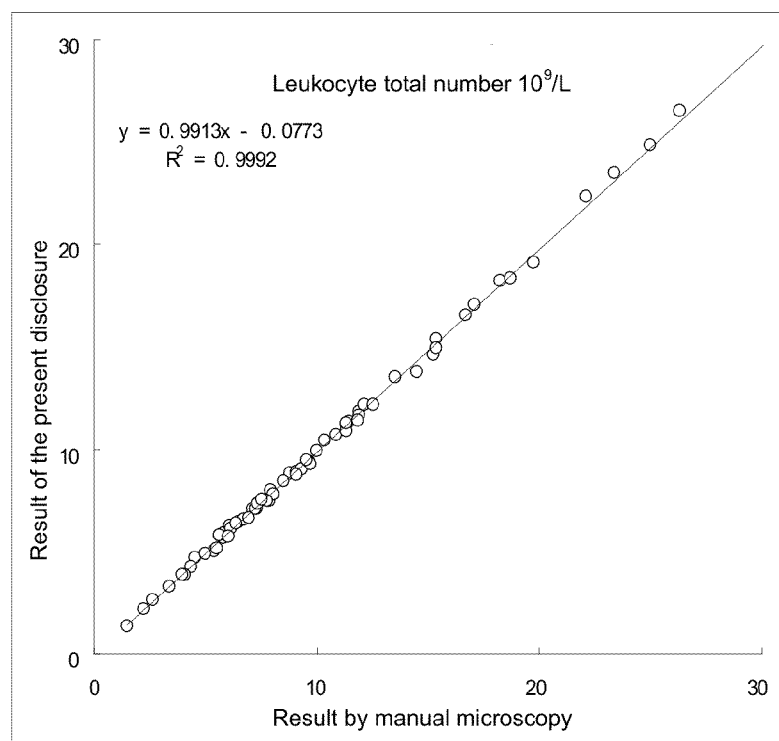
FIGS. 5A-E show the correlation between the results of differentiation and counting of leukocytes obtained using the reagent for differentiating and counting leukocytes according to one embodiment of the present disclosure and the results obtained by manual microscopy using the conventional Wright-Giemsa stain method as described in Example 4.
Figure 5B:
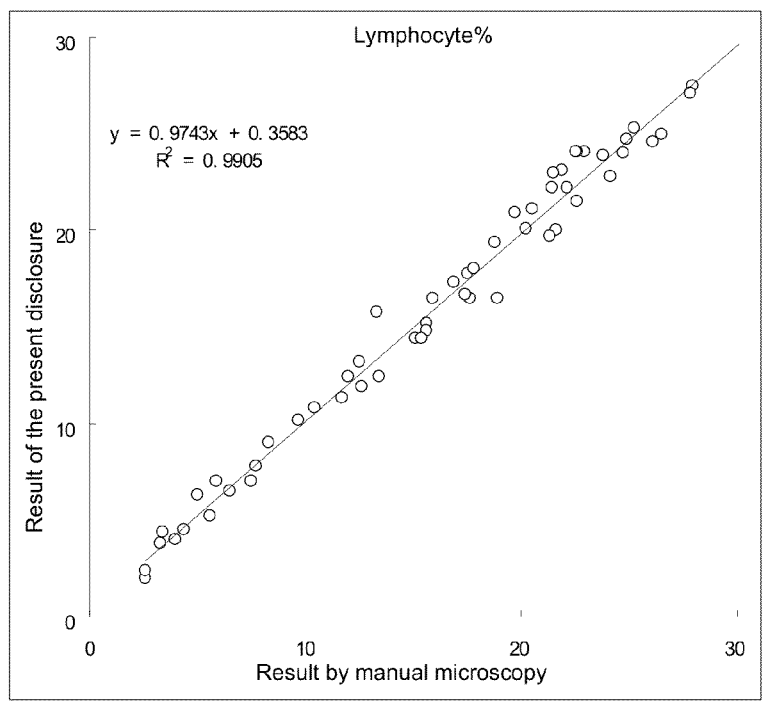
Figure 5C:
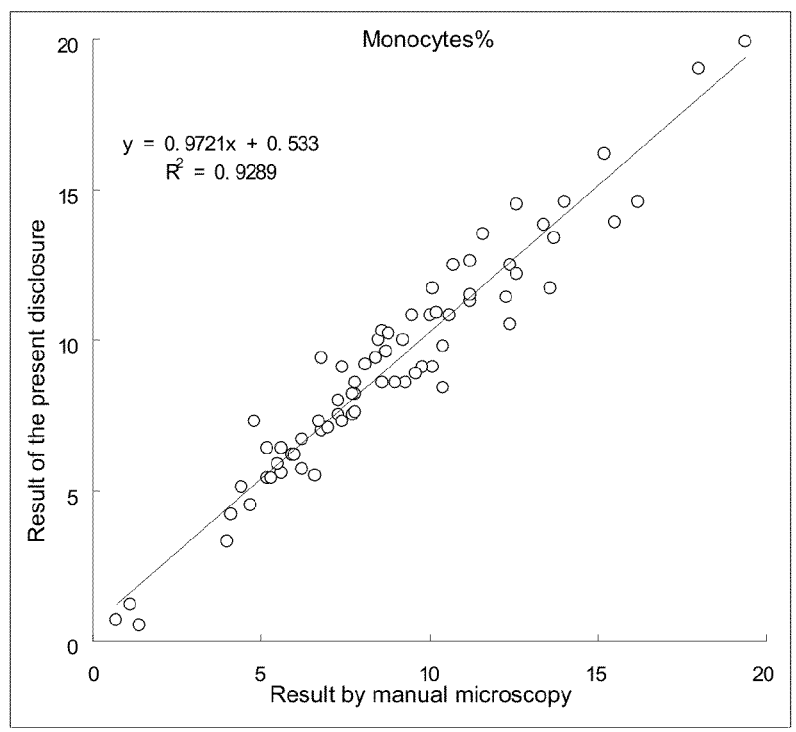
Figure 5D:
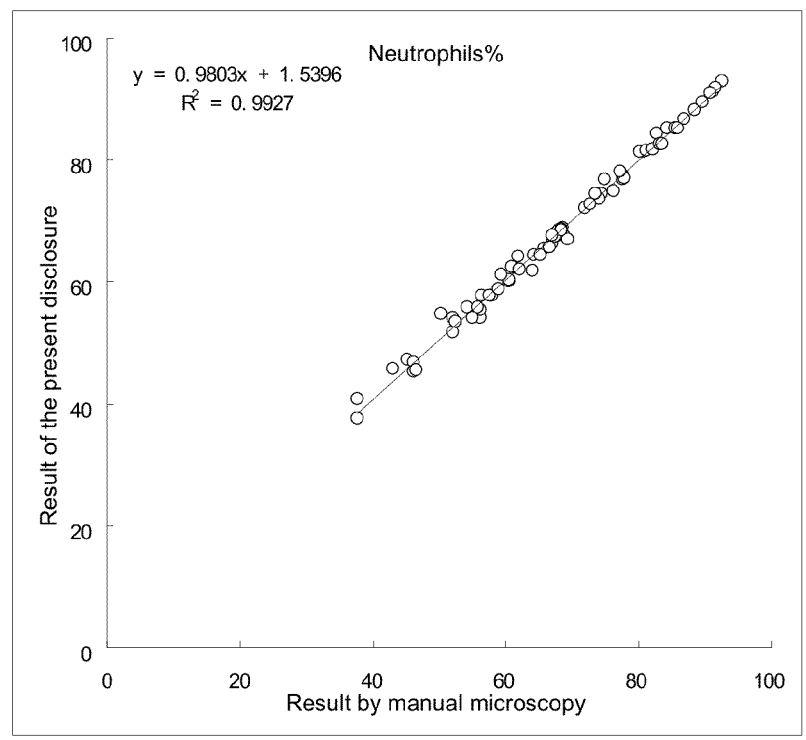
Figure 5E:
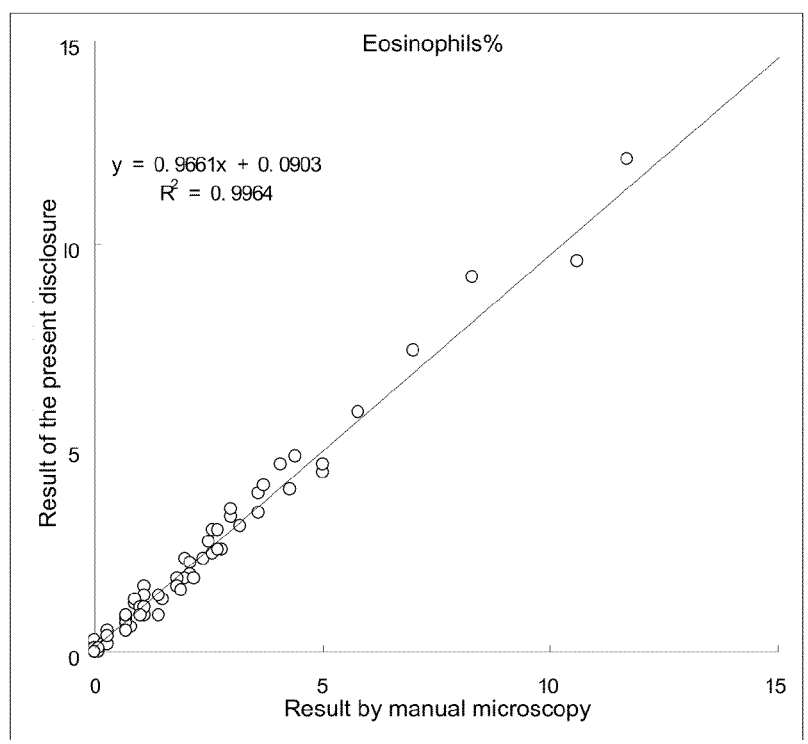

20 μl of fresh anti-coagulation blood sample having a relatively higher percentage of abnormal lymphocytes (the percentage of abnormal lymphocytes was 3.0% as detected by microscopic examination) was added into 1 ml of the aforesaid Reagent C, mixed for 15 seconds while the temperature was kept at 45° C., then leukocytes were detected using the laser flow cytometry method (light source: red semiconductor laser, wavelength 640 nm). Side fluorescence at the detection angle of 90° was used to detect the fluorescence intensity information of the leukocytes, and side-scattered light at the detection angle of 90° was used to detect the side-scattered light intensity information of the leukocytes. The result is as shown in FIG. 4, a 2-dimensional scattergram formed by plotting fluorescence intensity against side-scattered light intensity, from which it can be seen that besides the normal lymphocytes, monocytes, neutrophils, basophils and eosinophils, there exhibits an obvious occurrence of abnormal lymphocytes above the normal lymphocytes and monocytes. Calculated by manual delimitation of the abnormal lymphocyte population in the scattergram, the percentage of abnormal lymphocytes is 2.6%, which is close to the percentage detected by microscopic examination.

Example 4

Reagent D for differentiating and counting leukocytes was formulated which comprises the following dyeing liquid I and hemolytic agent II:

Dyeing Liquid I

| | |
|---|---|
| The compound of the above structural formula D | 10 ppm |

The dye was dissolved and stored in glycol.

Hemolytic Agent II

| | |
|---|---|
| laurylisoquinolinium bromide | 0.2 g/L |
| polyoxyethylene (25) cetyl ether | 1.5 g/L |
| sodium citrate | 2.0 g/L |
| ethanol | 50 g/L |
| HEPES | 3 g/L |

The above hemolytic agent was dissolved in 1 L of water and adjusted to pH 7.0 using sodium hydroxide.

Fifty tubes of fresh anti-coagulation blood were selected, and lymphocytes, monocytes, neutrophils and eosinophils were differentiated and counted by the following procedure.

20 μl of the aforesaid dyeing liquid I and 20 μl of blood sample from each of the fifty tubes were added into 1 ml of the aforesaid hemolytic agent II, mixed for 20 seconds while the temperature was kept at 40° C., then leukocytes were detected using the laser flow cytometry method (light source: red semiconductor laser, wavelength 640 nm). Side fluorescence at the detection angle of 90° was used to detect the fluorescence intensity information of the leukocytes, and side-scattered light at the detection angle of 90° was used to detect the side-scattered light intensity information of the leukocytes. Lymphocytes, monocytes, neutrophils and eosinophils were differentiated and counted by manual delimitation of the respective populations in the 2-dimensional scattergram formed by plotting fluorescence intensity against side-scattered light intensity. The results obtained were compared to those obtained by manual microscopy using the conventional Wright-Giemsa stain method and correlation analysis was conducted.

The results are as shown in FIG. 5(A-E) in which each of results for leukocyte total number (A), lymphocyte % (B), monocyte % (C), neutrophil % (D) and eosinophil % (E) shows a good correlation with the corresponding result obtained by manual microscopy using the conventional Wright-Giemsa stain method.

Example 5

Reagent E for differentiating and counting leukocytes was formulated with the following ingredients:

| | |
|---|---|
| The compound of the above structural formula E | 0.5 ppm |
| myristyltrimethyl ammonium chloride | 0.3 g/L |
| polyoxyethylene (23) lauryl ether | 1.3 g/L |
| orthophthalic acid | 3.0 g/L |
| Tris | 2.4/L | the pH being adjusted to 7.0 with hydrochloric acid.

Another reagent—Reagent F for differentiating and counting leukocytes was formulated with the following ingredients:

| | |
|---|---|
| The compound of the above structural formula E | 0.5 ppm |
| myristyltrimethyl ammonium chloride | 0.3 g/L |
| polyoxyethylene (23) lauryl ether | 1.3 g/L |
| orthophthalic acid | 3.0 g/L |
| 2-phenoxyethanol | 3 g/L |
| Tris | 2.4 g/L | the pH being adjusted to 7.0 with hydrochloric acid.

One tube of fresh anti-coagulation blood was selected and stored at 4° C. in the refrigerator. The blood was sampled at 4, 36 and 72 hours after storage and detected using Reagent E and Reagent F, respectively, according to the detection method as described in Example 1. The scattergrams for the detection results are as shown in FIGS. 6(A-F), wherein FIGS. 6(A), (B) and (C) show the detection results for the blood samples stored for 4, 36 and 72 hours respectively, obtained using Reagent E without alcohol added, while FIGS. 6(D), (E) and (F) show the detection results for the blood samples stored for 4, 36 and 72 hours respectively, obtained using Reagent F with alcohol added. Comparison of the detection results obtained using Reagent E without alcohol added to those obtained using Reagent F with alcohol added indicates that the result of differentiation by Reagent E of the respective leukocyte subtypes, especially lymphocyte and monocyte, in the blood samples stored for different periods of time shows a marked decline with the ongoing aging of the blood, while Reagent F that contains a certain concentration of alcohol achieves a better result of differentiation than that with Reagent E with no alcohol added. With regard to use of Reagent F to differentiate leukocytes in fresh blood (FIG. 6D) and 72-hour aged blood (FIG. 6F), it can be seen from the scattergrams that the results of differentiation of the respective leukocyte subtypes, especially lymphocyte and monocyte, are well maintained.

Example 6

Reagent G for differentiating and counting leukocytes was formulated with the following ingredients:

| The compound of the above structural formula F octylisoquinolinium bromide | 0.5 ppm |
| --- | --- |
| polyoxyethylene (30) cetyl ether | 0.6 g/L |
| sodium citrate | 1.6 g/L |
| | 2.0 g/L |
| Tris | 1.2 g/L | the pH being adjusted to 7.0 with hydrochloric acid.

20 μl of fresh anti-coagulation blood sample having a relatively higher percentage of both immature granulocytes (IG) and abnormal lymphocytes (IG % was 5.0% and the percentage of abnormal lymphocytes was 2.4% as detected by microscopic examination) was added into 1 ml of the aforesaid Reagent G, mixed for 15 seconds while the temperature was kept at 42° C., then leukocytes were detected using the laser flow cytometry method (light source: red semiconductor laser, wavelength 640 nm). Side fluorescence at the detection angle of 90° was used to detect the fluorescence intensity information of the leukocytes, and side-scattered light at the detection angle of 90° was used to detect the side-scattered light intensity information of the leukocytes. The result is as shown in FIG. 7, a 2-dimensional scattergram formed by plotting fluorescence intensity against side-scattered light intensity, from which it can be seen that besides the normal lymphocytes, monocytes, neutrophils, basophils and eosinophils, there exhibits an obvious occurrence of immature granulocytes above the normal neutrophils. Calculated by manual delimitation of the immature granulocyte population in the scattergram, the IG % is 5.3%, which is close to the percentage detected by microscopic examination. It can also be seen that there exhibits an obvious occurrence of abnormal lymphocytes above the normal lymphocytes and monocytes. Calculated by manual delimitation of the abnormal lymphocyte population in the scattergram, the percentage of abnormal lymphocytes is 2.6%, which is close to the percentage by microscopic examination.

Example 7

Reagent H for differentiating and counting leukocytes was formulated with the following ingredients:

| The compound of the above structural formula A laurylisoquinolinium bromide | 0.5 ppm |
| --- | --- |
| polyoxyethylene (25) cetyl ether | 0.2 g/L |
| 2-phenoxyethanol | 1.0 g/L |
| | 2.0 g/L |
| Tris | 1.2 g/L | the pH being adjusted to 7.0 with hydrochloric acid.

Figure 8:
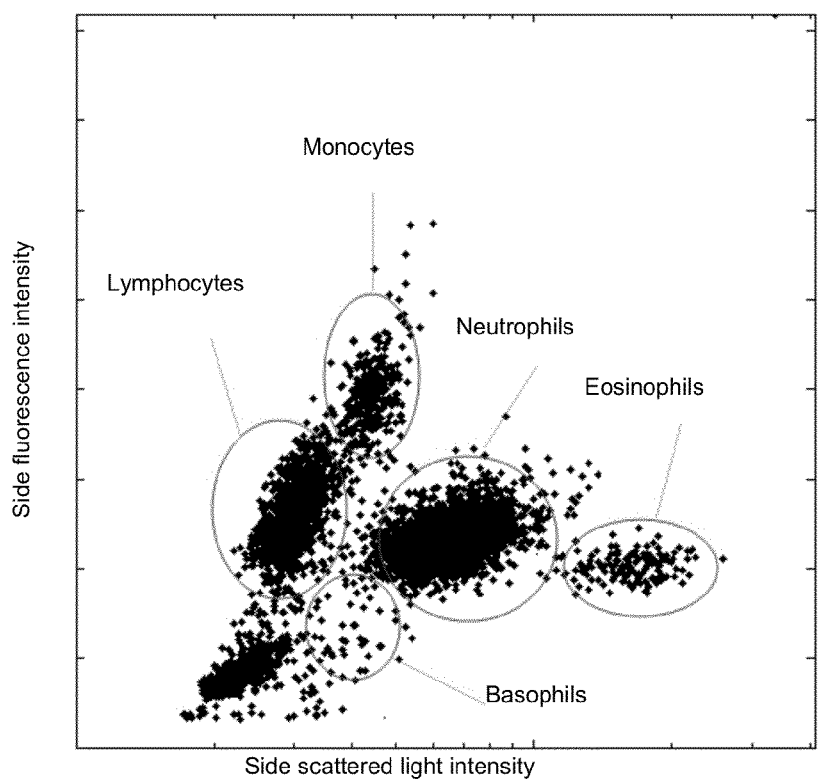
FIG. 8 is a scattergram formed by plotting the side fluorescence intensity against side-scattered light intensity of blood measured using the reagent for differentiating and counting leukocytes according to one embodiment as described in Example 7.

20 μl of fresh anti-coagulation blood sample was added into 1 ml of the aforesaid Reagent H, mixed for 20 seconds while the temperature was kept at 40° C., then leukocytes were detected using the laser flow cytometry method (light source: red semiconductor laser, wavelength 640 nm). Side fluorescence at the detection angle of 90° was used to detect the fluorescence intensity information of the leukocytes, and side-scattered light at the detection angle of 90° was used to detect the side-scattered light intensity information of the leukocytes. The result is as shown in FIG. 8, in which leukocytes are differentiated into five subtypes: lymphocyte, monocyte, neutrophil, eosinophil and basophil.

Example 8

Reagent I for differentiating and counting leukocytes was formulated with the following ingredients:

| The compound of the above structural formula C myristylquinolinium bromide | 0.5 ppm |
| --- | --- |
| polyoxyethylene (23) lauryl ether | 0.15 g/L |
| 2-phenoxyethanol | 1.5 g/L |
| | 2.0 g/L |
| HEPES | 2.0 g/L | the pH being adjusted to 7.0 with sodium hydroxide.

Figure 9:
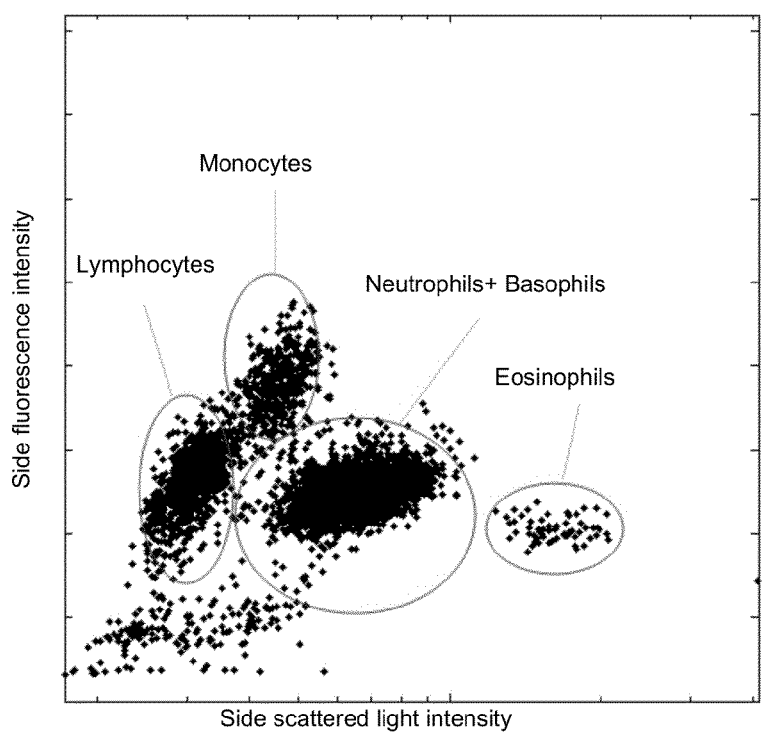
FIG. 9 is a scattergram formed by plotting the side fluorescence intensity against side-scattered light intensity of blood measured using the reagent for differentiating and counting leukocytes according to one embodiment as described in Example 8.

20 μl of fresh anti-coagulation blood sample was added into 1 ml of the aforesaid Reagent I, mixed for 20 seconds while the temperature was kept at 40° C., then leukocytes were detected using the laser flow cytometry method (light source: red semiconductor laser, wavelength 640 nm). Side fluorescence at the detection angle of 90° was used to detect the fluorescence intensity information of the leukocytes, and side-scattered light at the detection angle of 90° was used to detect the side-scattered light intensity information of the leukocytes. The result is as shown in FIG. 9, in which leukocytes are differentiated into at least four groups: three groupings corresponding to monocyte, lymphocyte and eosinophil respectively and one grouping corresponding to neutrophil plus basophil.

Example 9

Reagent J for differentiating and counting leukocytes was formulated with the following ingredients:

| The compound of the above structural formula C myristylquinolinium bromide | 0.5 ppm |
| --- | --- |
| polyoxyethylene (23) lauryl ether | 0.15 g/L |
| 2-phenoxyethanol | 1.5 g/L |
| | 2.0 g/L |
| HEPES | 2.0 g/L | the pH being adjusted to 7.0 with sodium hydroxide.

Figure 10:
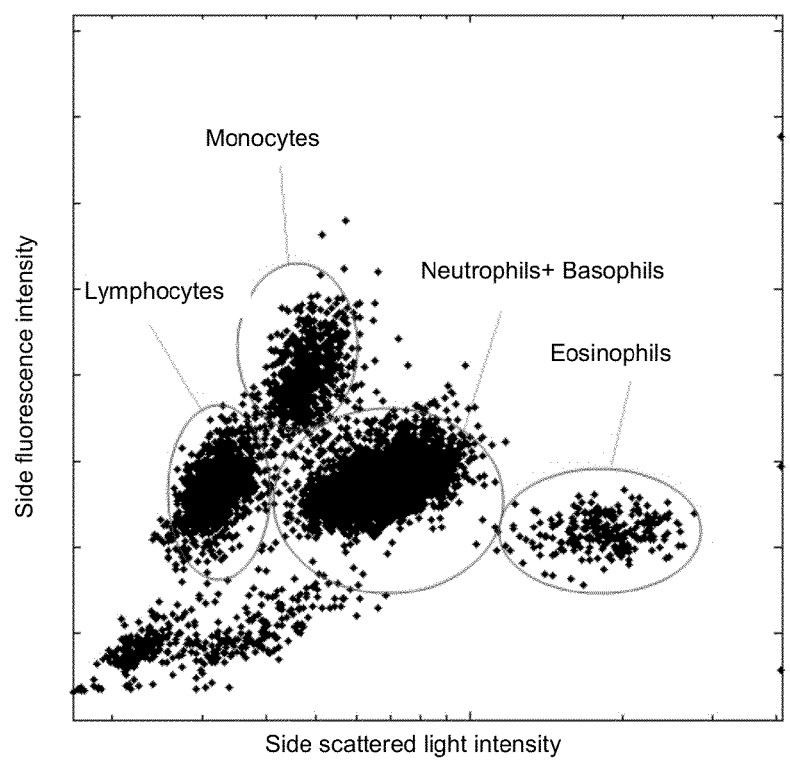
FIG. 10 is a scattergram formed by plotting the side fluorescence intensity against side-scattered light intensity of blood measured using the reagent for differentiating and counting leukocytes according to one embodiment as described in Example 9.

20 μl of fresh anti-coagulation blood sample was added into 1 ml of the aforesaid Reagent I, mixed for 20 seconds while the temperature was kept at 40° C., then leukocytes were detected using the laser flow cytometry method (light source: red semiconductor laser, wavelength 640 nm). Side fluorescence at the detection angle of 90° was used to detect the fluorescence intensity information of the leukocytes, and side-scattered light at the detection angle of 90° was used to detect the side-scattered light intensity information of the leukocytes. The result is as shown in FIG. 10, in which leukocytes are differentiated into at least four groups: three groupings corresponding to monocyte, lymphocyte and eosinophil respectively and one grouping corresponding to neutrophil plus basophil.

Although the present disclosure has been illustrated by way of the above embodiments and particular examples thereof, it will be appreciated by those skilled in the art that various changes, alterations and modifications may be made to the present disclosure without departing from the spirit and scope of the present disclosure as claimed.

The invention claimed is:

1. A reagent for differentiating and counting leukocytes, said reagent comprises:

(1) cationic cyanine compounds selected from those having the following general formulae I and II;

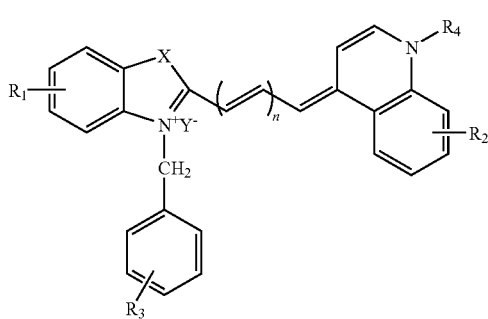

wherein
n is 1, 2 or 3;
X is C(CH$_3$)$_2$, O, S or Se;
R$_1$ and R$_2$ are each independently selected from H, C$_{1-18}$alkyl, —C$_{1-6}$alkyl-OR$_5$ or a halogen;
R$_3$ is H, C$_{1-18}$alkyl, OR$_5$, —C$_{1-6}$alkyl-OR$_5$, COOR$_5$, NO$_2$, CN or a halogen;
R$_4$ is C$_{1-18}$alkyl, —C$_{1-6}$alkyl-OR$_5$, benzyl or a halogen, wherein said benzyl is optionally substituted with a substituent selected from a halogen, hydroxyl, sulfhydryl, cyano, nitro, alkyl, aryl, alkyloxy, haloalkyl, amino, alkylamino, amido or carboxyl;
R$_5$ is H or C$_{1-18}$alkyl; and
Y$^-$ is an anion; or

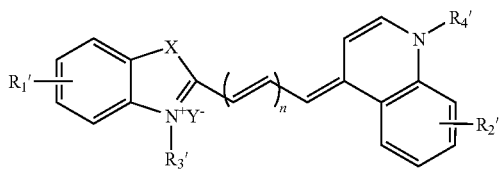

wherein
n is 1, 2 or 3;
X is C(CH$_3$)$_2$, O, S or Se;
R$_1$' and R$_2$' are each independently selected from H, OH, C$_{1-18}$alkyl, C$_{1-6}$alkylOR$_5$', C$_{1-18}$alkylsulfonyl, phenyl or a halogen;
R$_3$' and R$_4$' are each independently selected from C$_{1-18}$alkylCOOR$_6$', C$_{1-18}$alkylOR$_6$' or benzyl, wherein said benzyl is optionally substituted with a substituent selected from a halogen, hydroxyl, sulfhydryl, cyano, nitro, alkyl, aryl, alkyloxy, haloalkyl, amino, alkylamino, amido or carboxyl, provided that R$_3$' and R$_4$' are not simultaneously benzyl, and R$_4$' is not C$_{1-18}$alkylOR$_6$' when R$_3$' is benzyl;
R$_5$' is C$_{1-18}$alkyl or H;
R$_6$' is C$_{1-18}$alkyl, H or phenyl, wherein said phenyl is optionally substituted with a substituent selected from a halogen, hydroxyl, sulfhydryl, cyano, nitro, alkyl, aryl, alkyloxy, haloalkyl, amino, alkylamino, amido or carboxyl; and Y$^-$ is an anion;

(2) cationic surfactants that are quinolinium salt-type cationic surfactants having the following general formulae III and/or IV:

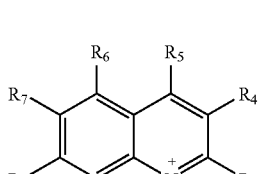

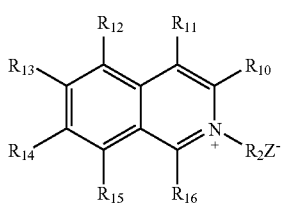

wherein
R$_1$ and R$_2$ are each independently selected from C$_{6-18}$alkyl and C$_{6-18}$haloalkyl;
R$_3$ to R$_{16}$ are each independently selected from H, OH, C$_{1-4}$alkyl, C$_{1-4}$alkyloxy and sulphonyl; and
Z$^-$ is a halogen ion;

(3) at least one nonionic surfactant; and (4) at least one anionic compound selected from those having one or more carboxyl or sulphonyl groups.

2. The reagent according to claim 1, wherein said compounds of the general formula I are selected from the following:

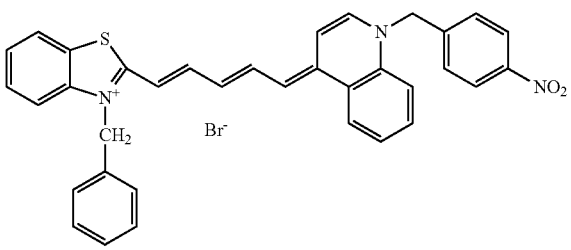

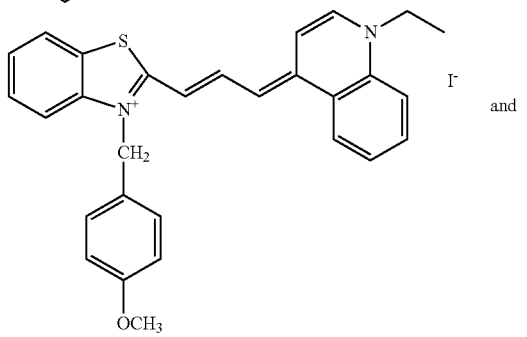

and

-continued

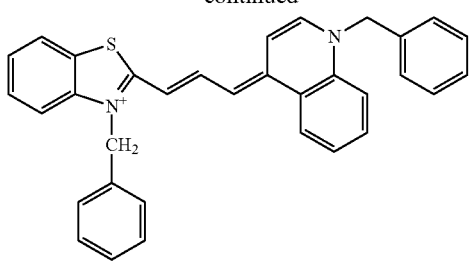

and said compounds of the general formula II are selected from the following:

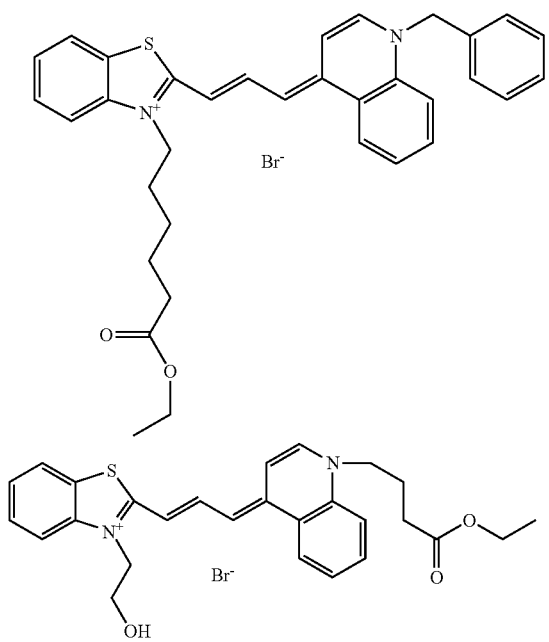

and

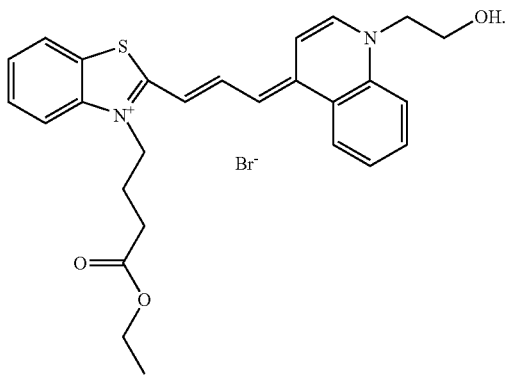

3. The reagent according to claim 1, wherein said cationic surfactants are selected from octylquinolinium bromide, octylisoquinolinium bromide, decylquinolinium bromide, decylisoquinolinium bromide, laurylquinolinium bromide, laurylisoquinolinium bromide, myristylquinolinium bromide, myristylisoquinolinium bromide, and combinations thereof.

4. The reagent according to claim 1, wherein said nonionic surfactants are at least one selected from the polyoxyethylene-type nonionic surfactants having the following general formula VI or combinations thereof:

$$R_1-R_2-(CH_2CH_2O)_n-H \quad \text{VI}$$

wherein
$R_1$ is $C_{8-23}$alkyl or $C_{8-23}$alkenyl, specifically such straight alkyls as octyl, decyl, lauryl, myristyl, cetyl or stearyl, and more specifically such straight alkyls as lauryl, myristyl or cetyl;

$R_2$ is —O—,

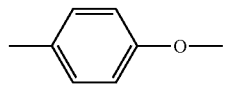

or —COO—; and
n is an integer of 8-30.

5. The reagent according to claim 4, wherein said nonionic surfactants are selected from polyoxyethylene (23) lauryl ether, polyoxyethylene (25) cetyl ether, polyoxyethylene (30) cetyl ether, and combinations thereof.

6. The reagent according to claim 1, wherein said anionic compounds having one or more carboxyl or sulphonyl groups are selected from formic acid, acetic acid, benzoic acid, citric acid, malic acid, orthophthalic acid, benzenesulfonic acid, α-naphthalenesulphonic acid and taurine, and alkali metal salts thereof.

7. The reagent according to claim 1, wherein said reagent optionally comprises at least one alcohol compound.

8. The reagent according to claim 7, wherein said alcohol compound is selected from methanol, ethanol, isopropanol, n-butanol, benzyl alcohol and 2-phenoxyethanol.

9. A kit for differentiating and counting leukocytes, wherein said kit comprises the reagent for differentiating and counting leukocytes according to claim 1, wherein said reagent can either be a reagent system comprising a single component or a reagent system comprising two or more reagent components.

10. The reagent according to claim 1, further comprising:
a buffering agent to maintain the pH of the reagent at between about pH 6 to about pH 8.

11. The reagent according to claim 1, wherein the reagent has an osmotic pressure of between 10 mOsm to 100 mOsm.

12. A reagent for differentiating and counting leukocytes, said reagent comprises:
(1) cationic cyanine compounds selected from those having the following general formulae I and II;

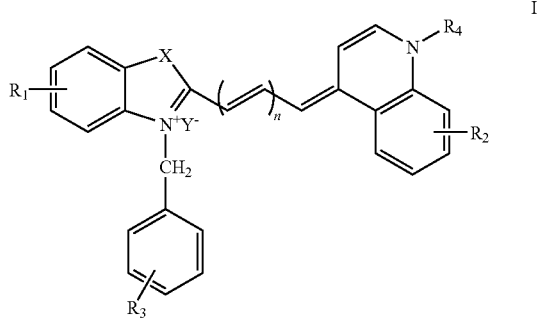

wherein
n is 1, 2 or 3;
X is $C(CH_3)_2$, O, S or Se;
$R_1$ and $R_2$ are each independently selected from H, $C_{1-18}$alkyl, —$C_{1-6}$alkyl-$OR_5$ or a halogen;

$R_3$ is H, $C_{1-18}$alkyl, $OR_5$, —$C_{1-6}$alkyl-$OR_5$, $COOR_5$, $NO_2$, CN or a halogen;

$R_4$ is $C_{1-18}$alkyl, —$C_{1-6}$alkyl-$OR_5$, benzyl or a halogen, wherein said benzyl is optionally substituted with a substituent selected from a halogen, hydroxyl, sulfhydryl, cyano, nitro, alkyl, aryl, alkyloxy, haloalkyl, amino, alkylamino, amido or carboxyl;

$R_5$ is H or $C_{1-18}$alkyl; and $Y^-$ is an anion; or

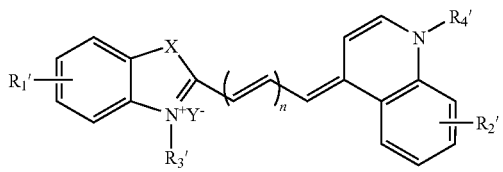

II wherein
n is 1, 2 or 3;
X is $C(CH_3)_2$, O, S or Se;
$R_1'$ and $R_2'$ are each independently selected from H, OH, $C_{1-18}$alkyl, $C_{1-18}$alkylsulfonyl, phenyl or a halogen;
$R_3'$ and $R_4'$ are each independently selected from $C_{1-18}$alkylCOOR$_6'$, $C_{1-18}$alkylOR$_6'$ or benzyl, wherein said benzyl is optionally substituted with a substituent selected from a halogen, hydroxyl, sulfhydryl, cyano, nitro, alkyl, aryl, alkyloxy, haloalkyl, amino, alkylamino, amido or carboxyl, provided that $R_3'$ and $R_4'$ are not simultaneously benzyl, and $R_4'$ is not $C_{1-18}$alkylOR$_6'$ when $R_3'$ is benzyl;
$R_5'$ is $C_{1-18}$alkyl or H;
$R_6'$ is $C_{1-18}$alkyl, H or phenyl, wherein said phenyl is optionally substituted with a substituent selected from a halogen, hydroxyl, sulfhydryl, cyano, nitro, alkyl, aryl, alkyloxy, haloalkyl, amino, alkylamino, amido or carboxyl; and $Y^-$ is an anion;

(2) cationic surfactants that are quinolinium salt-type cationic surfactants having the following general formulae III and/or IV:

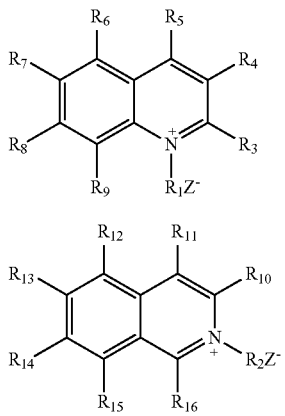

wherein
$R_1$ and $R_2$ are each independently selected from $C_{6-18}$alkyl and $C_{6-18}$haloalkyl;
$R_3$ to $R_{16}$ are each independently selected from H, OH, $C_{1-4}$alkyl, $C_{1-4}$alkyloxy and sulphonyl; and
$Z^-$ is a halogen ion; and (3) at least one nonionic surfactant.

13. The reagent according to claim 12, wherein said compounds of the general formula I are selected from the following:

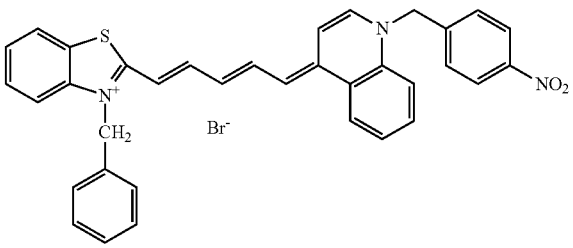

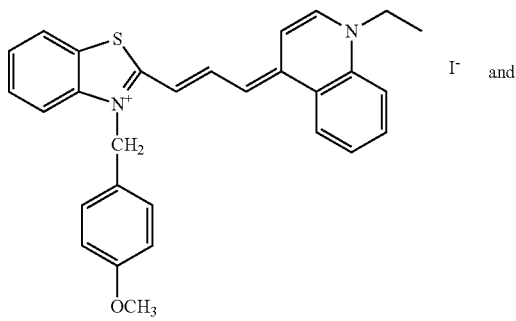

and

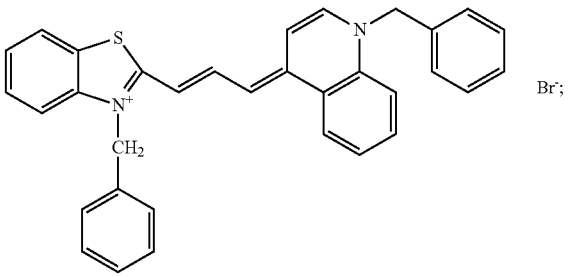

and said compounds of the general formula II are selected from the following:

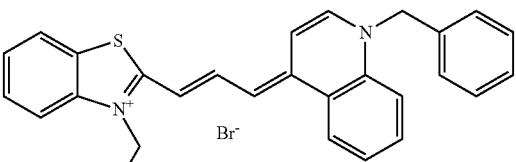

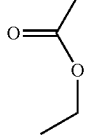

-continued

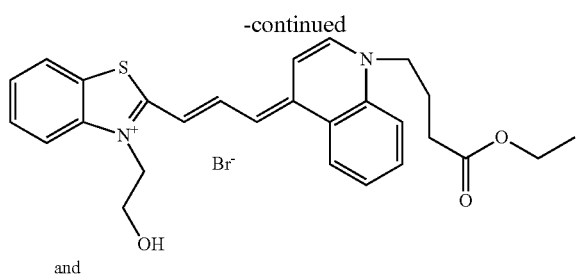

and

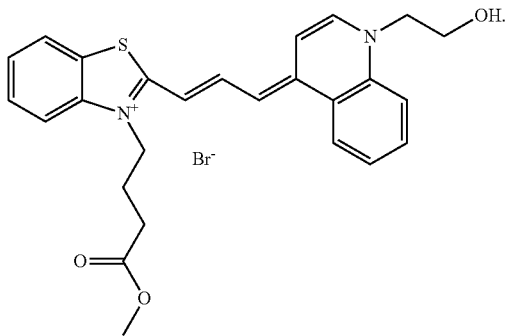

14. The reagent according to claim 12, wherein said cationic surfactants are selected from octylquinolinium bromide, octylisoquinolinium bromide, decylquinolinium bromide, decylisoquinolinium bromide, laurylquinolinium bromide, laurylisoquinolinium bromide, myristylquinolinium bromide, myristylisoquinolinium bromide, cetylquinolinium bromide, cetylisoquinolinium bromide, and combinations thereof.

15. The reagent according to claim 12, wherein said nonionic surfactants are at least one selected from the polyoxyethylene-type nonionic surfactants having the following general formula VI or combinations thereof:

$$R_1-R_2-(CH_2CH_2O)_n-H \qquad VI$$

wherein
  $R_1$ is $C_{8-23}$alkyl or $C_{8-23}$alkenyl, specifically such straight alkyls as octyl, decyl, lauryl, myristyl, cetyl or stearyl, and more specifically such straight alkyls as lauryl, myristyl or cetyl;
  $R_2$ is —O—,

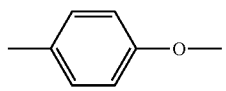

or —COO—; and
  n is an integer of 8-30.

16. The reagent according to claim 15, wherein said nonionic surfactants are selected from polyoxyethylene (23) lauryl ether, polyoxyethylene (25) cetyl ether, polyoxyethylene (30) cetyl ether, and combinations thereof.

17. The reagent according to claim 12, wherein said reagent optionally comprises at least one alcohol compound.

18. The reagent according to claim 17, wherein said alcohol compound is selected from methanol, ethanol, isopropanol, n-butanol, benzyl alcohol and 2-phenoxyethanol.

19. A kit for differentiating and counting leukocytes, wherein said kit comprises the reagent for differentiating and counting leukocytes according to claim 12, wherein said reagent can either be a reagent system comprising a single component or a reagent system comprising two or more reagent components.

20. The reagent according to claim 12, further comprising:
  a buffering agent to maintain the pH of the reagent at between about pH 6 to about pH 8.

21. The reagent according to claim 12, wherein the reagent has an osmotic pressure of between 10 mOsm to 100 mOsm.

* * * * *